United States Patent
Barbee et al.

(10) Patent No.: US 9,346,063 B2
(45) Date of Patent: May 24, 2016

(54) CENTRIFUGE AND METHOD FOR LOADING A DEVICE

(71) Applicant: LIFE TECHNOLOGIES CORPORATION, Carlsbad, CA (US)

(72) Inventors: Kristopher Barbee, East Haven, CT (US); Ryan Jones, New Haven, CT (US); Sean McCusker, New Haven, CT (US); Maximilian Carpino, Uncasville, CT (US); John Leamon, Guilford, CT (US); Jonathan Schultz, Oxford, MA (US)

(73) Assignee: Life Technologies Corporation, Carlsbad, CA (US)

( * ) Notice: Subject to any disclaimer, the term of this patent is extended or adjusted under 35 U.S.C. 154(b) by 323 days.

(21) Appl. No.: 13/828,633

(22) Filed: Mar. 14, 2013

(65) Prior Publication Data

US 2013/0288873 A1    Oct. 31, 2013

Related U.S. Application Data

(60) Provisional application No. 61/640,243, filed on Apr. 30, 2012, provisional application No. 61/668,938, filed on Jul. 6, 2012, provisional application No. 61/700,003, filed on Sep. 12, 2012.

(51) Int. Cl.
 *B04B 13/00* (2006.01)
 *B04B 5/04* (2006.01)
 (Continued)

(52) U.S. Cl.
 CPC ............... *B04B 13/00* (2013.01); *B04B 5/0421* (2013.01); *G01N 35/00693* (2013.01); *G01N 35/1011* (2013.01); *G01N 2035/00495* (2013.01); *G01N 2035/103* (2013.01); *G01N 2035/1013* (2013.01)

(58) Field of Classification Search
 CPC .... B04B 5/0414; B04B 5/0421; B04B 13/00; B01D 21/26
 See application file for complete search history.

(56) References Cited

U.S. PATENT DOCUMENTS 3,951,334 A * 4/1976 Fleming et al. .................. 494/20
4,484,907 A * 11/1984 Sheeran, Jr. ..................... 494/85
5,045,047 A * 9/1991 Hutchins et al. ................ 494/17

(Continued)

FOREIGN PATENT DOCUMENTS

EP    1348966    5/2006

OTHER PUBLICATIONS

International Preliminary Report on Patentability for International Application No. PCT/US2013/031640 mailed Nov. 4, 2014, 11 pages.

(Continued)

*Primary Examiner* — Charles Cooley
*Assistant Examiner* — Shuyis S Liu

(57) ABSTRACT

An apparatus includes a robotic system providing movement in three orthogonal directions to an arm operable to receive a pipette tip and to facilitate movement of fluid into and out of the pipette tip. In addition, the apparatus can include a tray for receiving pipette tips, receptacles for receiving tubes, an apparatus for forming an emulsion, a device for forming particles that include copies of the polynucleotide, a device for enriching the particles and an apparatus for loading such particles onto a sensor array. The apparatus can further include receptacles for holding containers of reagent solutions. Optionally, the robot can include a gripper arm in addition to the pipette receiving arm.

20 Claims, 27 Drawing Sheets

(51) Int. Cl.
*G01N 35/00* (2006.01)
*G01N 35/10* (2006.01)

(56) References Cited

U.S. PATENT DOCUMENTS 6,350,225 B1 * 2/2002 Sheeran et al. ............... 494/12
2005/0130173 A1 * 6/2005 Leamon et al. ................ 435/6

OTHER PUBLICATIONS

PCT/US2013/031640, "International Search Report of the International Searching Authority and Written Opinion", Oct. 15, 2013, 18 pages.
PCT/US2013/031640, "Partial Search Report", Jul. 18, 2013, 2 pages.

* cited by examiner

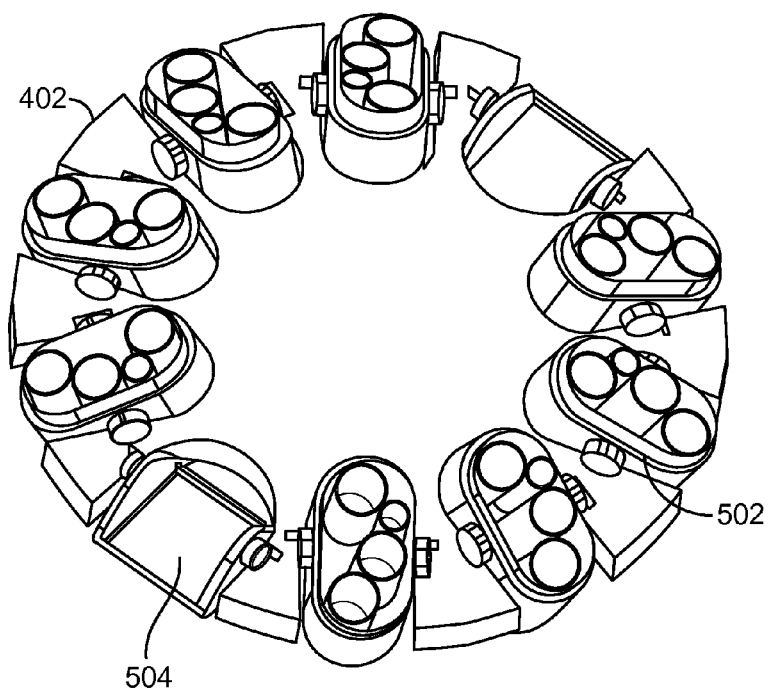
FIG. 5
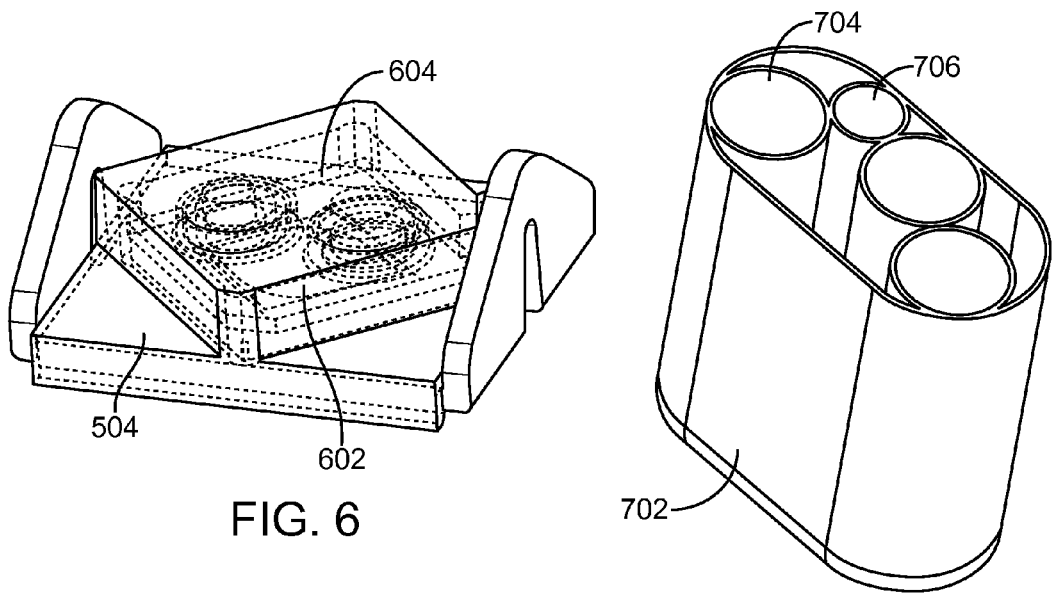
FIG. 6
FIG. 7

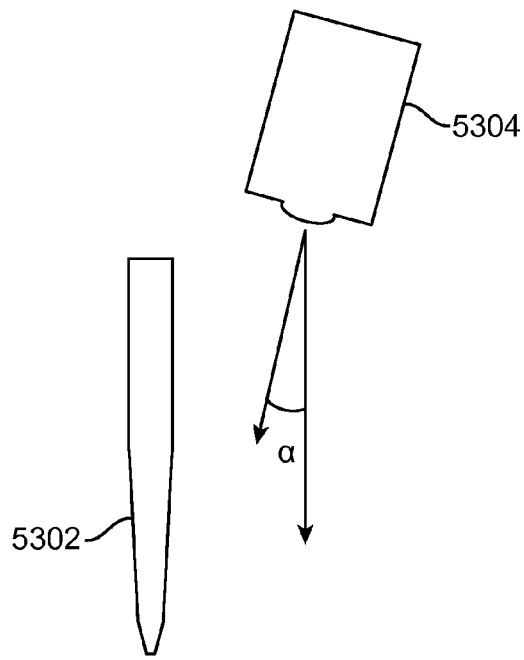
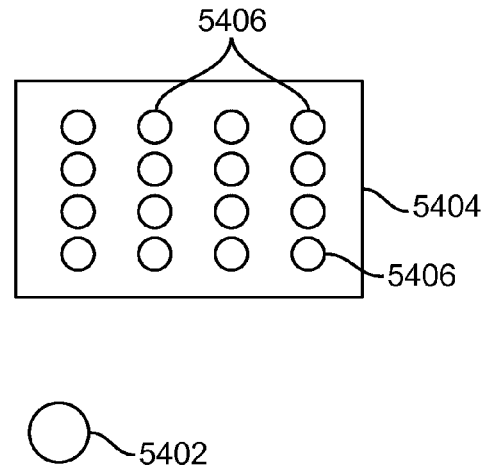
FIG. 53          FIG. 54
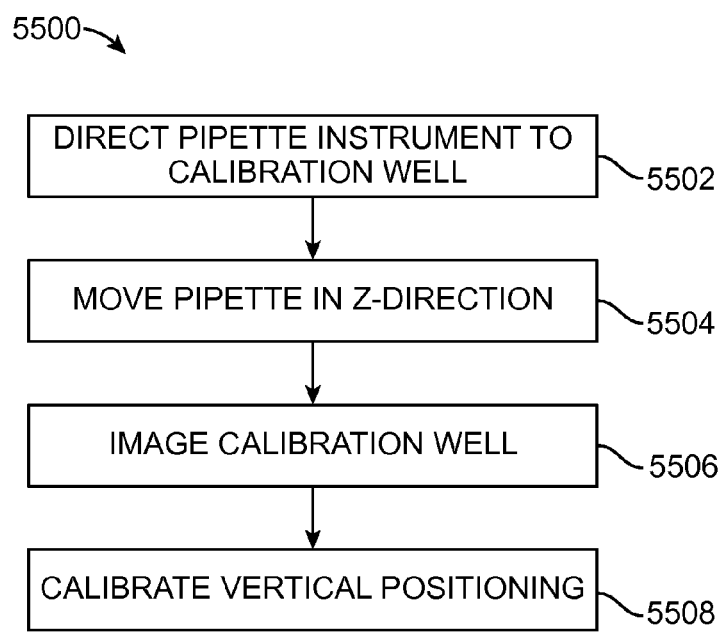
FIG. 55

CENTRIFUGE AND METHOD FOR LOADING A DEVICE

CROSS-REFERENCE TO RELATED APPLICATION(S)

This application claims benefit of U.S. Provisional Application No. 61/640,243, filed Apr. 30, 2012, which is incorporated herein by reference in its entirety.

This application claims benefit of U.S. Provisional Application No. 61/668,938, filed Jul. 6, 2012, which is incorporated herein by reference in its entirety.

This application claims benefit of U.S. Provisional Application No. 61/700,003, filed Sep. 12, 2012, which is incorporated herein by reference in its entirety.

FIELD OF THE DISCLOSURE

This disclosure, in general, relates to apparatuses and methods for loading sensor substrates with amplified polynucleotide particles.

BACKGROUND

Recent advances in molecular biology, particularly sequencing technologies, rely on the deposition of biomolecule-enhanced particles on the surface of a sensing apparatus, such as an array of sensors on a substrate. In particular, technologies that detect nucleotide addition through minute changes in pH within a well rely on the deposition of particles including copies of the target polynucleotide. Such particles having copies of the target polynucleotide can be formed using techniques such as emulsion polymerase chain reaction (PCR).

SUMMARY

In a first aspect, a method of calibrating a system includes attaching a pipette tip to a syringe pump coupled to a translation device, initiating fluid flow through the pipette tip, moving the pipette tip toward a contact surface with the translation device, and calibrating the system based on a position of the translation device when the syringe pump detects a pressure change.

In a second aspect, a centrifuge device includes a motor operable to spin in a first direction and in a second direction opposite the first direction and a rotor coupled to a motor. The rotor is to spin within a plane in the first direction or the second direction responsive to the motor. The rotor has a recess and an axle projecting from a side of the recess. The centrifuge device further includes a carrier slidably and pivotally coupled to the axle. The carrier includes a first tab on a first side and a second tab on a second side. The carrier is to slide along the axle and to rotate about the axle out of the plane and engage the rotor with the first tab at a first angle in response to the rotor spinning in the first direction. The carrier is to slide along the axle and to rotate about the axle out of the plane and engage the rotor with the second tab at a second angle in response to the rotor spinning in the second direction.

In a third aspect, a method includes spinning a rotor within a plane in a first direction. A carrier is coupled to the rotor by an axle. The carrier slides along the axle and rotates about the axle to engage the rotor with a first tab at a first angle in response to the rotor spinning in the first direction. The method further includes spinning the rotor within the plane in a second direction. The carrier slides along the axle and rotates about the axle to engage the rotor with a second tab at a second angle in response to the rotor spinning in the second direction. The first angle is greater than the second angle.

In a fourth aspect, a centrifuge includes a rotor to spin within a plane, a carrier, an upper plate, and a first arm pivotally coupled at a first end to the upper plate. A second end of the first arm is pivotally coupled to the carrier. The centrifuge further includes a second arm pivotally coupled to the rotor at a first end. A second end of the second arm is pivotally coupled to the first arm at a position on the first arm between the first end and the second end of the first arm. An angle of the carrier relative to the plane changes responsive to position of the upper plate.

In a fifth aspect, a centrifuge includes a rotor to spin in a plane, a slinger positioned over a central axis of the rotor and including a receiving port and an arm including a distal opening in fluid communication with the receiving port, and a carrier block pivotally coupled to the rotor and including a receptacle for a tube. The carrier block weighted to position the tube in an approximate vertical position when the rotor is stationary and to position the tube at an angle with an opening of the tube directed to the distal opening of the slinger responsive to the rotor spinning.

In a sixth aspect, a method includes lowering a distal end of a pipette system to engage a pipette tip in a tray, raising the distal end, imaging the distal end with a camera, and comparing a characteristic derived from the image with an expected tip characteristic.

In a seventh aspect, a system includes a syringe pump to couple to a pipette tip, a translation device to move the pipette tip, an enrichment system, and a centrifuge device. The enrichment system includes a mixing tube and a magnetic device movable relative to the mixing tube. The centrifuge device includes a rotor and a bucket to secure a sequencing device. The translation device is to position the pipette tip proximal to the mixing tube and proximal to the sequencing device.

In an eighth aspect, a method for preparing a sequencing device includes transferring an aqueous dispersion including amplified particles to an enrichment tube using a translation device coupled to a syringe pump, enriching the amplified particles, transferring the enriched amplified particles to a sequencing device disposed on a tray of a centrifuge device, and centrifuging the sequencing device.

BRIEF DESCRIPTION OF THE DRAWINGS

The present disclosure may be better understood, and its numerous features and advantages made apparent to those skilled in the art by referencing the accompanying drawings.

FIG. 5 includes an illustration of exemplary centrifuge device.

FIG. 6 includes an illustration of exemplary array loading tray for use in the exemplary centrifuge illustrated in FIG. 5.

FIG. 7 includes an exemplary centrifuge bucket insert for use in the exemplary centrifuge illustrated in FIG. 5.

FIG. 52 and FIG. 53 include illustrations of exemplary imaging systems.

FIG. 54 includes an illustration of exemplary calibration tools.

FIGS. 55-57 include flow diagrams illustrating exemplary methods for calibrating a system.

The use of the same reference symbols in different drawings indicates similar or identical items.

DETAILED DESCRIPTION

In an exemplary embodiment, an apparatus includes a translation device providing movement in three orthogonal directions to an arm and syringe pump operable to receive a pipette tip and to facilitate movement of fluid into and out of the pipette tip. In addition, the apparatus can include a tray for receiving pipette tips, receptacles for receiving tubes, an apparatus for forming an emulsion, a device for forming particles that include copies of the polynucleotide, a device for enriching the particles, and an apparatus for loading such particles onto a sequencing device, such as a chip including a sensor array. The apparatus can further include receptacles for holding containers of reagent solutions. Optionally, the translation device can include a gripper arm in addition to the pipette receiving arm. In an example, the emulsion forming device includes a mixer, such as IKA Turrax device, or includes pipette functionality that can form an emulsion. In another example, the device facilitating the loading of the array includes a centrifuge. In addition, such a centrifuge can be useful for breaking emulsion and separating other solutions.

In an exemplary method, an apparatus receives a sample including one or more target polynucleotides, a solution including particles, and other reagents. The sample and particles are incorporated into an emulsion including an aqueous phase in which a polymerase chain reaction (PCR) can occur. The emulsion can be transferred to a thermocycling device to undergo a prescribed set of thermal cycles. The emulsion can be broken utilizing chemical breaking, mechanical breaking, or a combination thereof. In particular, the emulsion can be broken using a combination of a centrifuge and emulsion breaking solutions. Optionally, the solution can be enriched to remove particles that do not include copies of the target polynucleotides. The solution can be loaded onto a sensor array, for example, using the centrifuge and pipetting particles onto the array.

Figure 1:
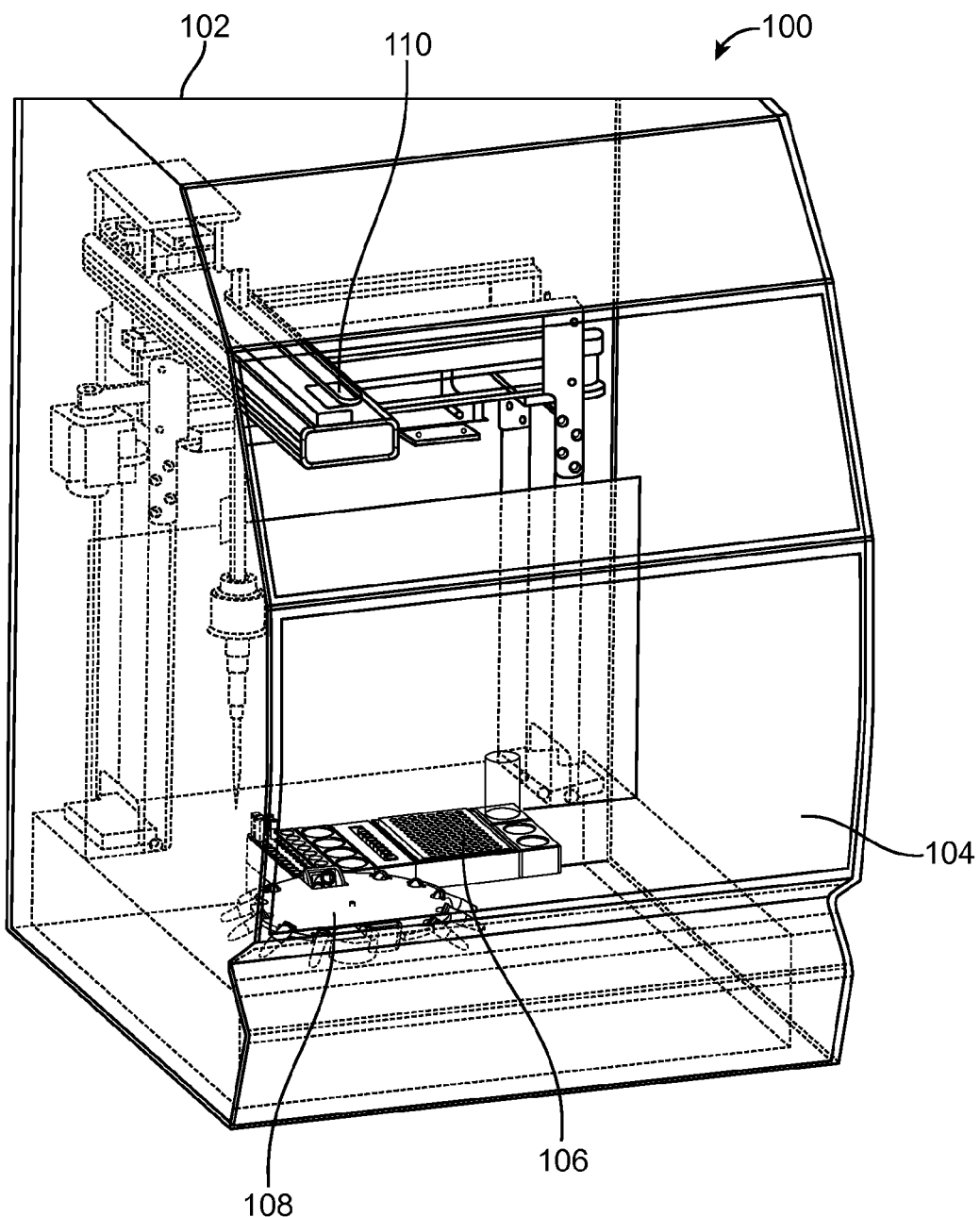
FIG. 1 includes an illustration of an exemplary apparatus for loading a sensor array with particles enhanced with copies of a target polynucleotide.

FIG. 1 includes an illustration of an exemplary apparatus 100 that includes an outer casing 102 and a door 104. Interior to the casing 102 is a translation device 110, such as an xyz-robot, having a pipette arm, a set of trays and apparatuses 106 for enriching or amplifying polynucleotide enhanced particles and a device, such as centrifuge 108, useful for loading a sequencing device, such as a chip with an array of sensors, with the enhanced particles. In particular, the translation device can move the pipette arm in three orthogonal directions. Optionally, the arm can also include a gripper.

Such a device can be dimensioned to reside on a bench top. The apparatus can also include a control circuitry and pumps useful in operating the translation device and pipetting system. The apparatus can also include a touchscreen user interface. In a further example, the apparatus can include a barcode scanner so that samples can be associated with a specific chip having a barcode indicative of a unique identification number.

In a further example, the apparatus can include a UV source for sanitizing the enclosure 102 following a run. In another example, the apparatus can include fume scrubber. In a further example, the translation device may include a second arm that may include a second pipetting system, a gripper or both. The door 104 may be a vertically sliding door for easy access to the entire deck, including components 106 and 108. In another example, the apparatus can include an air filtration system, such as a HEPA filter for air-flow in and charcoal filtration for air exiting the apparatus. The apparatus can include environmental controls to control temperature and humidity within the enclosure 102. One or more blocks or trays 106 can be temperature controlled, for example, chilling for polymerases and other enzymes or providing thermal cycling for PCR.

Figure 2:
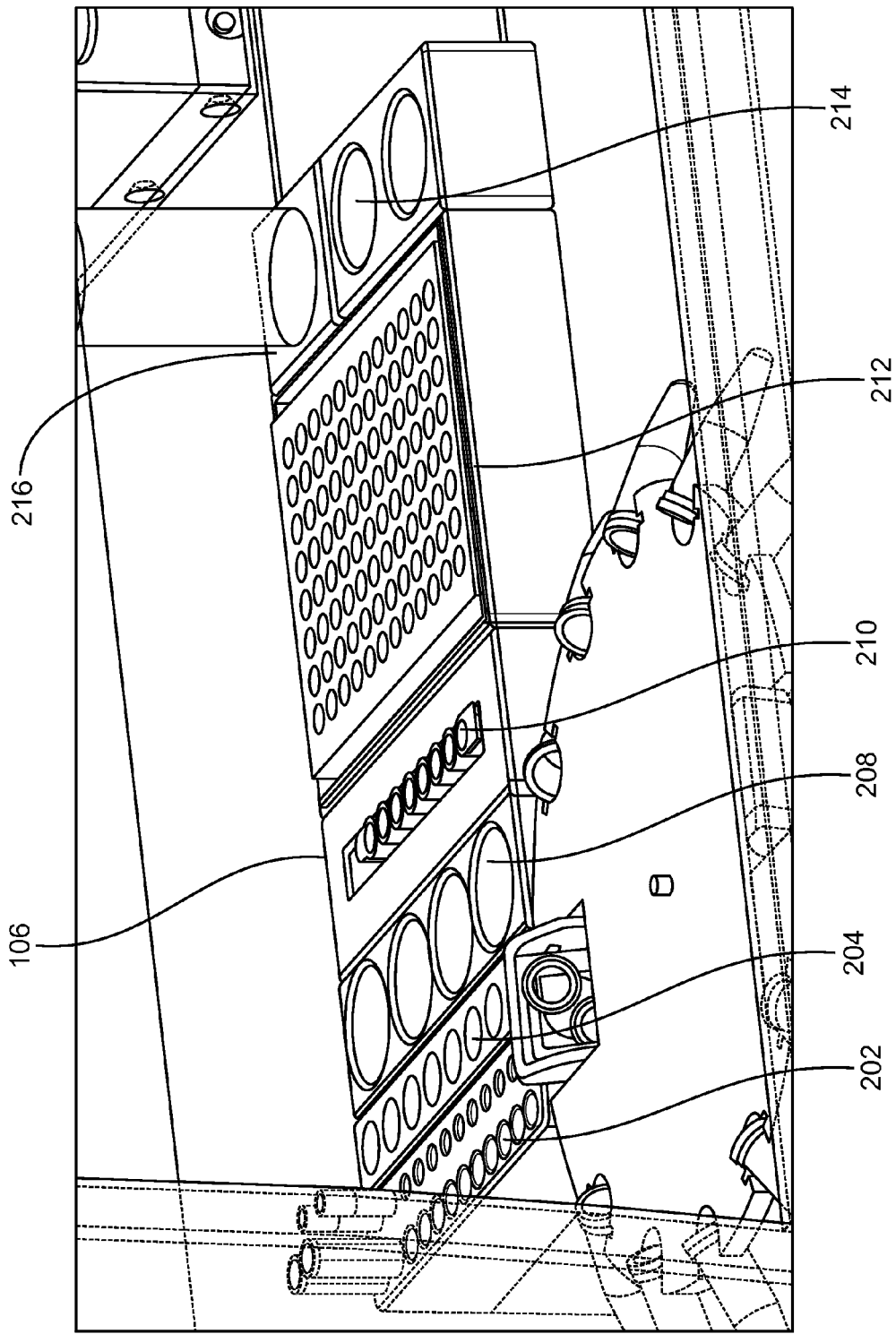
FIG. 2 includes an illustration of an exemplary set of devices for use in the exemplary apparatus of FIG. 1.

FIG. 2 includes an illustration of the set of devices 106. In an example, the apparatus includes a pipette tip rack 202, a reagent bottle rack 204, a larger volume reagent bottle rack, such as a 15 mL reagent bottle rack 208, an enrichment station 210, a thermocycling device 212, a waste container rack 214, and an emulsion generating station 216, such as an IKA Turrax device. In an example, a robotic arm including a syringe pump can select a pipette tip from the tip rack 202, draw reagents from one or more positions on racks 204 and 208 and form an emulsion using the emulsion generator 216. The emulsion can be distributed to a plate disposed on the thermocycling device 212. Following thermocycling, the emulsion can be broken by optionally pipetting the emulsion into containers on the centrifuge 108 and further optionally supplying additional reagents from one or more positions on reagent racks 204 and 208. Once the emulsion is broken, the sample can be separated from emulsion and applied to tubes within the enrichment system 210. After enrichment, the enriched particles can be applied to the sequencing device, such as a sensor array substrate, disposed on a tray of the centrifuge.

Figure 3:
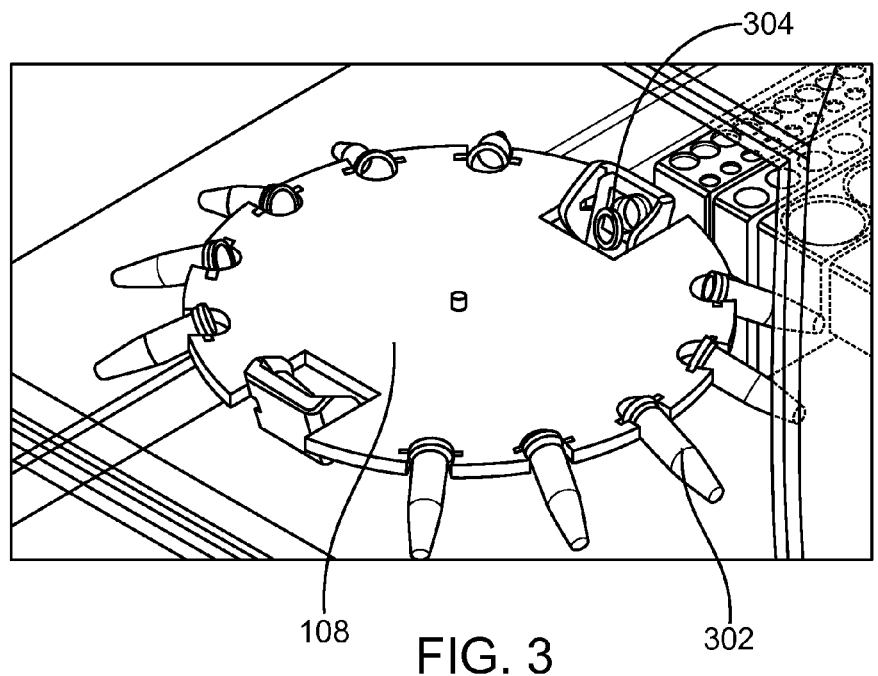
FIG. 3 includes an illustration of an exemplary centrifuge device useful in the exemplary apparatus of FIG. 1.

For example, FIG. 3 includes an illustration of a centrifuge 108. The centrifuge 108 includes tubes 302 for receiving liquid samples. In particular, such tubes 302 are useful for separating solutions and breaking emulsions. In addition, such a centrifuge 108 includes trays 304 to receive a chip or substrate including an array of sensors.

Figure 4:
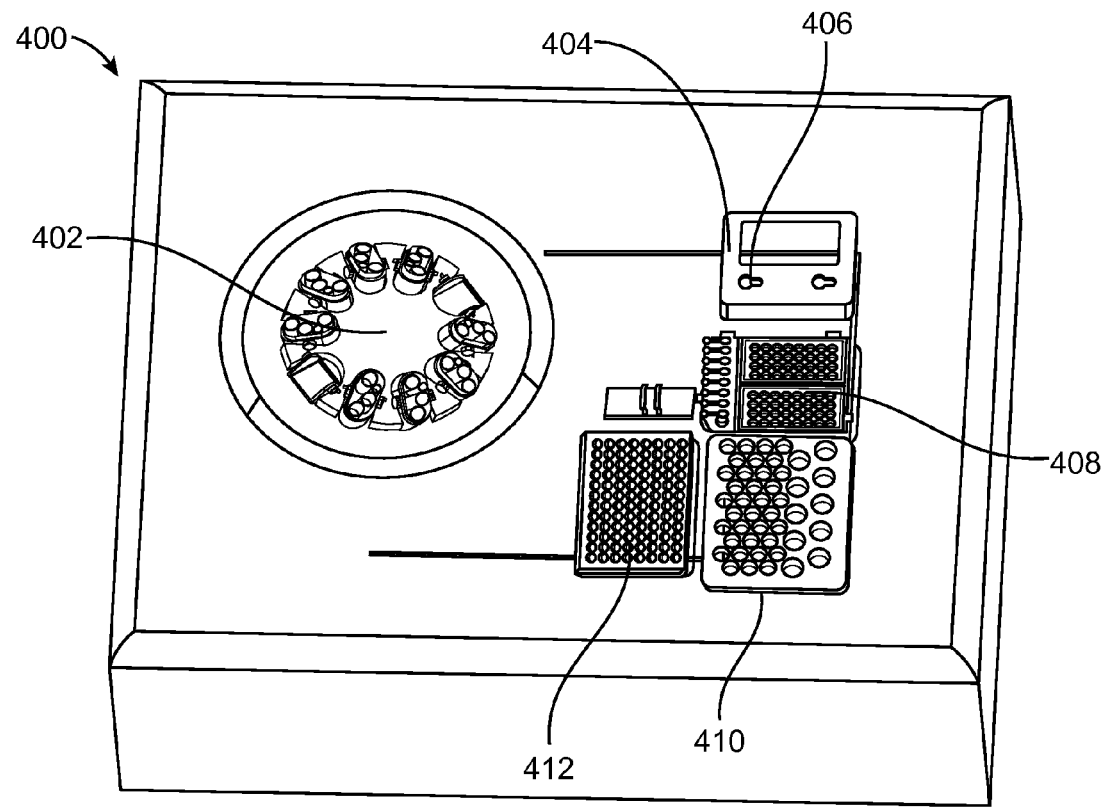
FIG. 4 includes an illustration of exemplary set of devices useful in an apparatus for loading a sensor array.

In an alternative example, a deck 400 illustrated in FIG. 4 includes a centrifuge 402, a receptacle 404 for receiving used pipette tips, a cartridge 408 for holding pipette tips and tubes, a further tray 410 to receive tubes, particularly those storing reagents, and the thermocycling plate 412. The receptacle 404 for receiving used pipette tips can include an eye 406. An arm attached to a used pipette can insert the pipette tips into the larger opening of the eye 406, slide the pipette tip under the smaller side of the eye 406 and rise up, dislodging the used pipette tip. In particular, the larger opening of the eye 406 is wider than the larger end of the pipette tip and the smaller opening of the eye 406 is smaller than the larger end of the pipette tip. The dislodged pipette tip can fall into a receptacle, such as the receptacle illustrated in FIG. 15.

As illustrated in FIG. 5, the centrifuge 402 includes buckets 502 for receiving inserts that can accommodate tubes of various dimensions and includes trays 504 for receiving a sequencing device, such as substrates or chips including a sensor array. For example, as illustrated in FIG. 6, trays 504 can receive a chip 602 on which an array of sensors is disposed. Optionally, an adapter 604 can be placed over the chip. Such an adapter 604 can be useful in securing the chip to the tray 504. In another example, the adapter 604 can be used during the loading process. In a particular example, the adapter 604 can include a funnel structure to guide fluid into an inlet port of the chip 602, allowing for less precision by the pipetting arm of the translation device.

In another example illustrated in FIG. 7, an insert 702 is configured to fit in a centrifuge bucket 502 and can include receptacles 704 or 706 having a variety of sizes for receiving tubes of different size. The insert 702 can be placed within centrifuge buckets 502 prior to the beginning of the process. Alternatively, one or more of the inserts 702 can be disposed in closer proximity to the trays and devices 404, 408, 410, or 412 of the system and such inserts 702 can be gripped and place in the centrifuge 402 following insertion of a tube within the insert 702.

Figure 8:
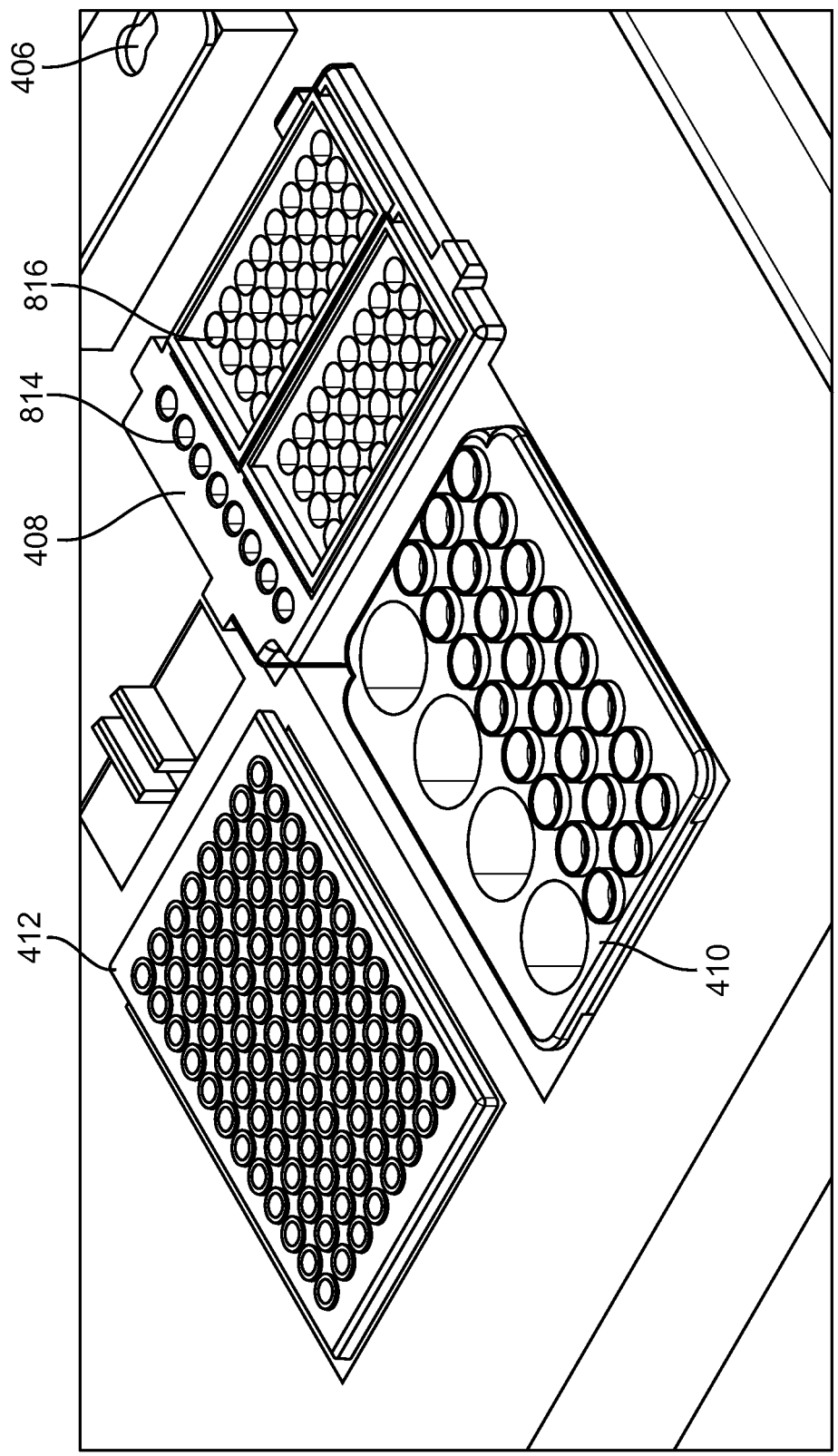
FIG. 8 includes an illustration of an exemplary set of devices for enhancing and enriching particles.

FIG. 8 includes a further illustration of an exemplary system deck. The system deck includes a pipette removal station including an eye 406, a pipette and tube receiving station 408, a reagent receiving station 410, and a thermocycler 412. The receiving station 408 can includes openings 814 to receive pipette tips and can receive trays of tubes 816. The reagent receiving station 410 can receive a variety of reagents in a variety of container sizes. As illustrated, the thermocycler 412 can be configured to receive 96 PCR tubes, a 96 well plate, or both.

Figure 9:
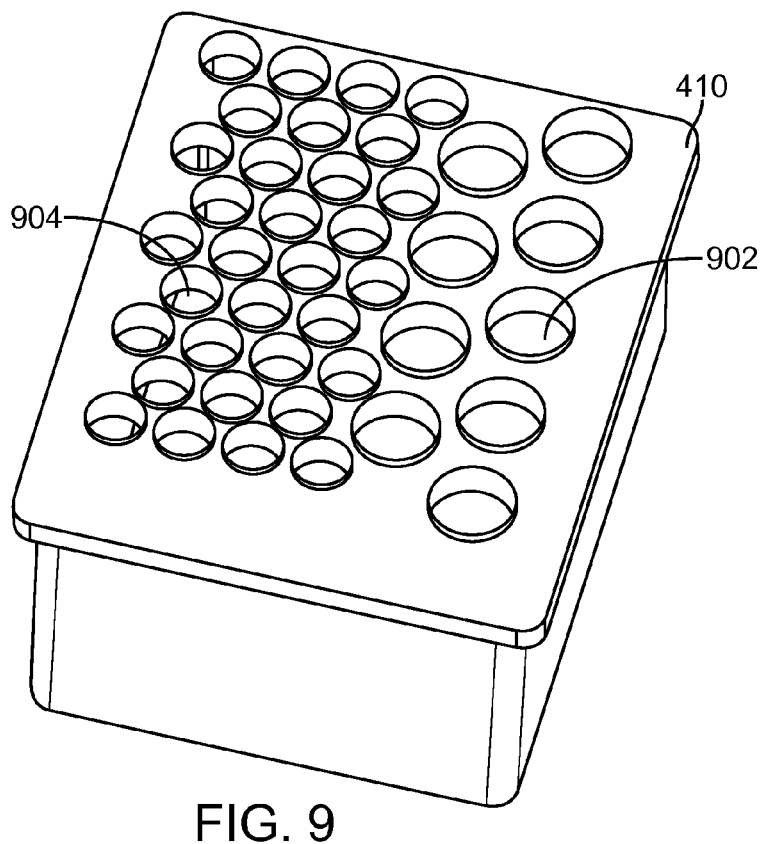
FIG. 9 and FIG. 10 include illustrations of exemplary reagent tube holders.
Figure 10:
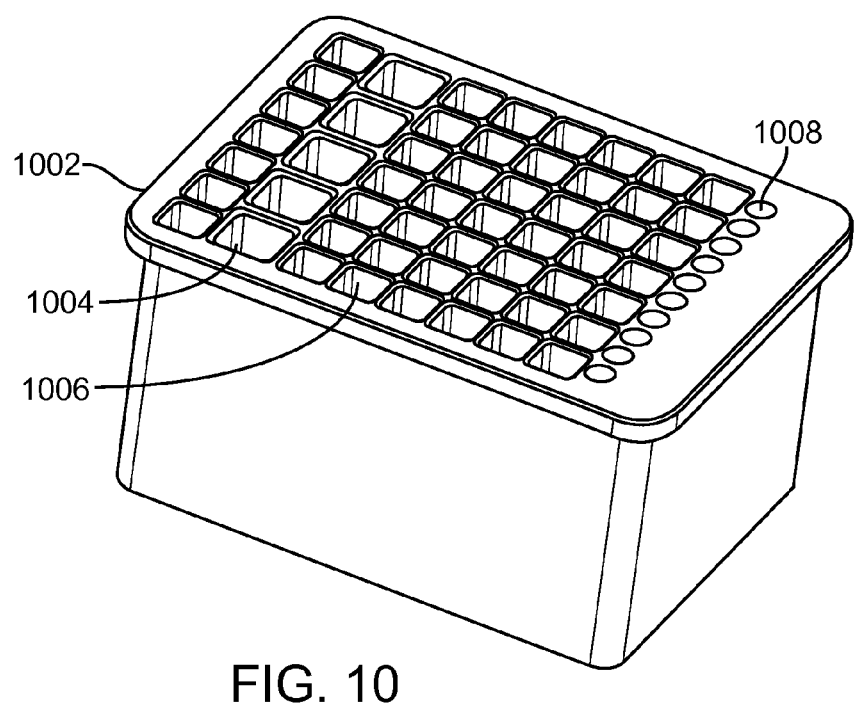

In a particular example illustrated in FIG. 9, a reagent tube holder 410 can include larger openings 902 to receive larger tubes of reagents, such as 5 mL tubes. The reagent tube holder 410 can also include openings 904 to receive smaller tubes, such as tubes having volumes in a range of 1.5 mL to 2 mL. The openings illustrated in FIG. 9 are illustrated as being circular. In another example, such openings can be square or a combination of openings can be included. For example, FIG. 10 is an illustration of an exemplary reagent holder 1002. The reagent holder 1002 can include larger openings 1004 and smaller openings 1006. In addition, openings 1008 to receive pipette tips are formed in the reagent tube holder 1002.

Figure 11:
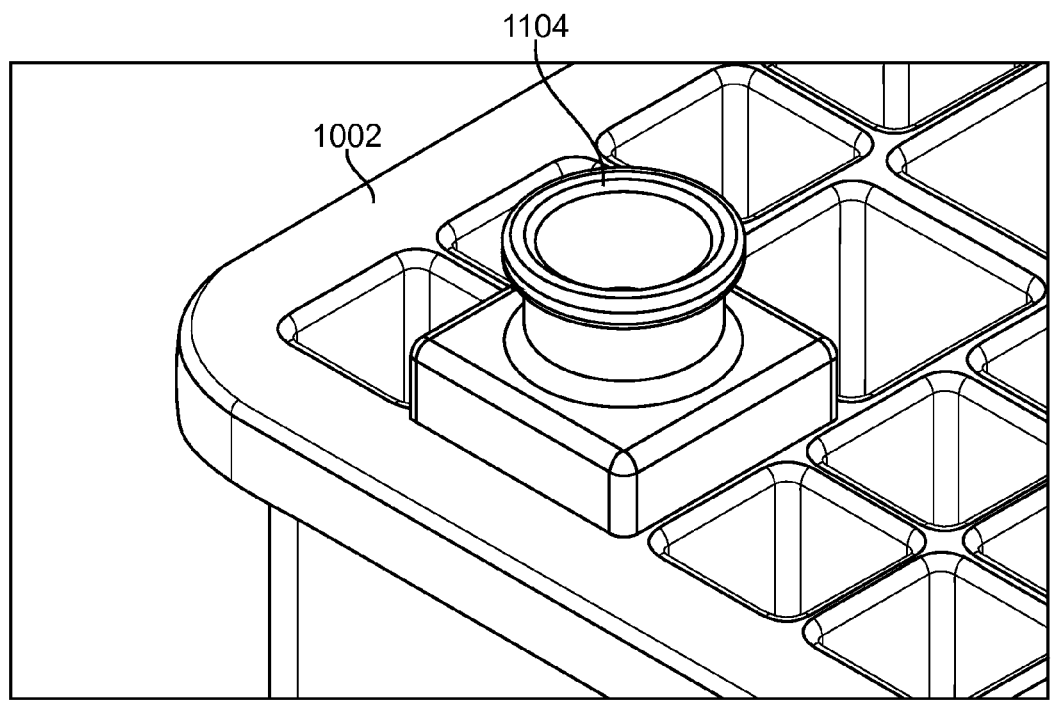
FIG. 11 and FIG. 12 include illustrations of an exemplary magnet system for use in an enrichment process.

In a particular example, particles amplified with multiple copies of target polynucleotides can be enriched to remove particles lacking polynucleotides from solution. In an example, such particles can be coupled with a magnetic particle and removed using a process that secures the magnetic particles within a well while particles that do not include target polynucleotides are flushed from the solution. In an example, such a method utilizes a magnet in an adjacent well to secure the magnetic particles. In a particular example, the above system can be adapted to utilizing a magnet. For example, FIG. 11 includes an illustration in which a magnet 1104 is configured to fit within one of the openings of the reagent tube holder 1002. In an example, the magnet 1104 is configured to fit within one of the larger openings 1004. Enrichment techniques can be carried out in adjacent smaller openings.

Figure 12:
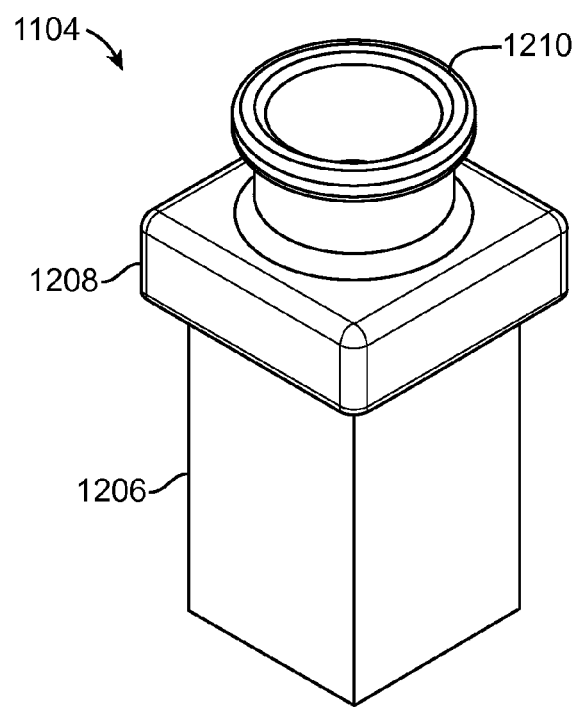

As illustrated in FIG. 12, the magnet 1104 can include a permanent magnetic 1206 and a cap 1208 disposed on the permanent magnetic material. The cap 1208 can include a rim 1210 to enable grippers to transfer the magnet to and from the reagent tube holder 1002.

Alternatively, a stationary magnet or a solenoid magnet can be used in place of the movable magnet. For example, a solenoid magnet can be placed below a tube holder and can be activated and deactivated to secure and release magnetic particles during the enrichment process.

Figure 13:
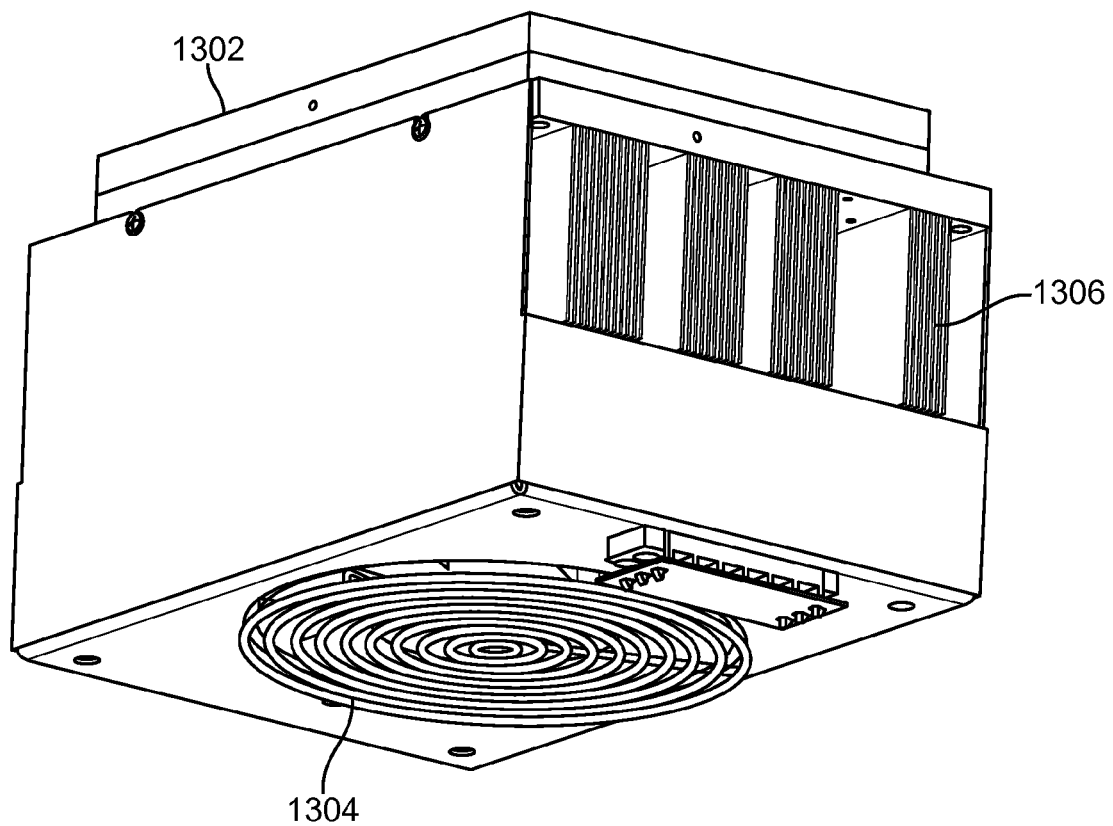
FIG. 13 includes an illustration of an exemplary thermocycling device.

In addition, the system includes a thermocycler. FIG. 13 is an illustration of exemplary thermocycling unit 1302, which includes a power and controller interface and includes both positive and negative thermal loads. For example, a positive thermal load includes the resistance heaters to heat samples. An exemplary negative load can include, for example, a fan 1304 and air inlet or cooling fins 1306 for cooling the resistive heaters during the thermal cycling.

Figure 14:
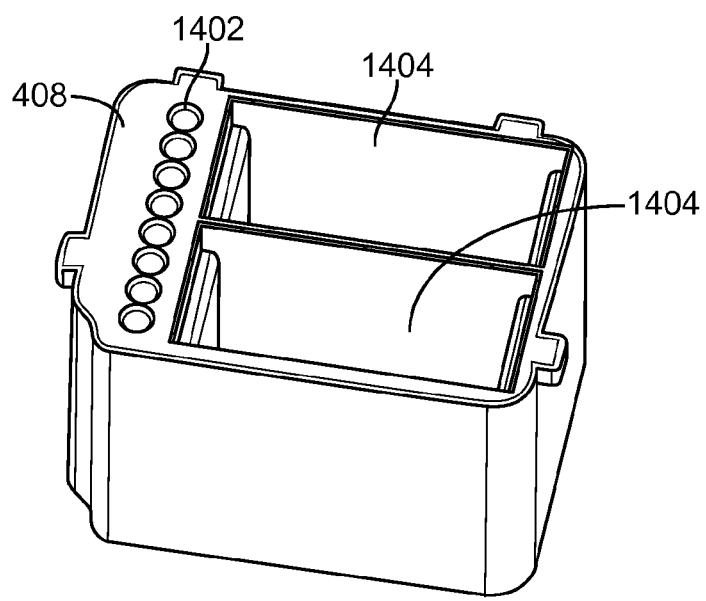
FIG. 14 includes an illustration of exemplary pipette holder.

An exemplary tube and pipette holder 408 is illustrated in FIG. 14 including openings 1402 for receiving pipette tips and openings 1404 for receiving a tray of tubes, such as PCR tubes. Optionally, the holder 408 can also include temperature controls, such as refrigeration components to maintained low temperatures for particular reagents, such as enzymes.

Figure 15:
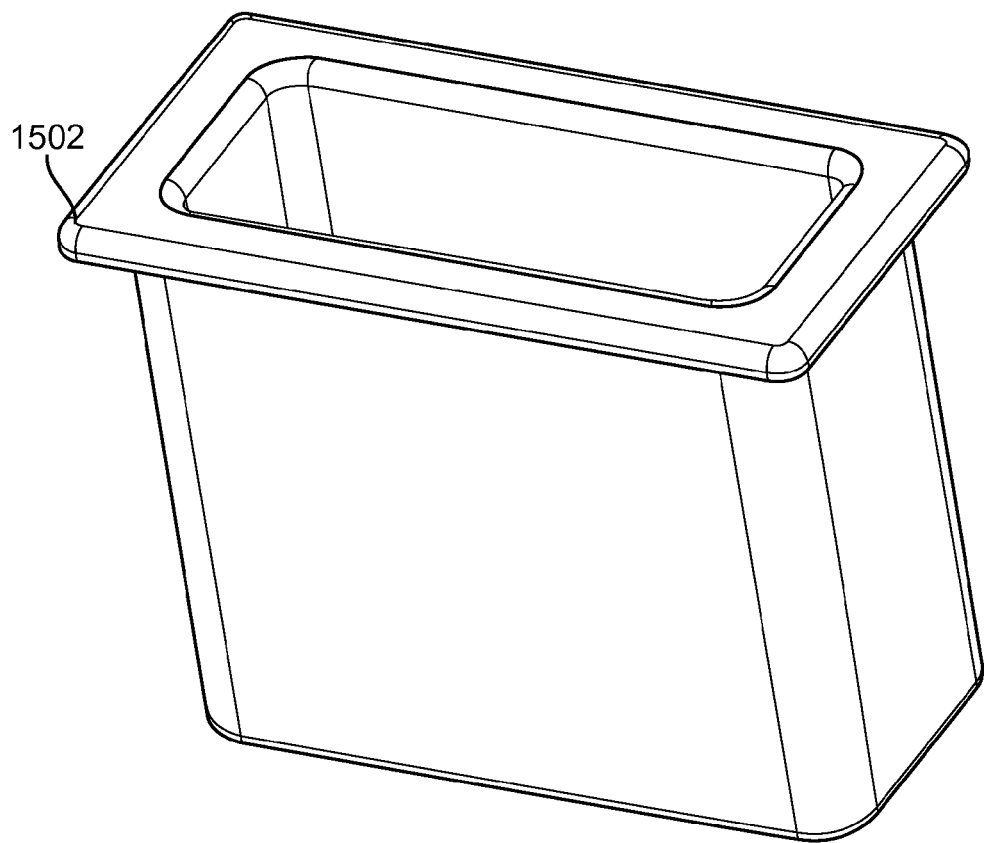
FIG. 15 includes an illustration of an exemplary receptacle for receiving used pipette tips.

In an additional example illustrated in FIG. 15, the receptacle 404 can include a removable receptacle, such as receptacle 1502 to receive used pipette tips and facilitate disposal of used pipette tips.

In an exemplary method, a sample solution including a set of target polynucleotides is provided. In addition, reagent solutions can include a solution including a dispersion of particles and a solution that is immiscible with aqueous solutions. An exemplary immiscible solution includes an oil. In addition, the system can include a reagent solution that includes enzymes, nucleotides, and various chemicals and cofactors useful in a polymerase chain reaction (PCR) or recombinase polymerase amplification (RPA). Alternatively, such enzymes and other components can be incorporated into the solution that includes the particles.

The particle solution, sample solution, optional component solution and the immiscible solution can be provided to an emulsion generating device. In an example, the emulsion generating device is a mechanical emulsion generating device, such as an IKA Turrax. In another example, the emulsion generating device includes a membrane and set of channel gaskets to generate an emulsion by flowing a mixture through channels of the channel gasket, back and forth through a membrane. In another example, the emulsion can be generated by a pipetting system oscillating immiscible solutions back-and-forth through a pipette tip to generate aqueous emulsion droplets within an immiscible continuous phase.

When using pipetting to generate an emulsion, an aqueous solution including particles, target polynucleotides and other PCR components is placed in a tube with an immiscible phase, such as an aqueous immiscible fluid, such as an oil. The solutions are drawn in and out of the pipette in rapid succession to generate an emulsion in which the aqueous phase forms discrete regions within a continuous oil phase. For example, the solution can be cycled at rates of 10 Hz to 10,000 Hz, such as rates of 100 Hz to 6000 Hz, rates of 500 Hz to 4000 Hz, or even rates of 500 Hz to 2500 Hz. The solutions can be cycled through the pipette tip between 3 and 1000 cycles, such as between 5 and 750 cycles, between 5 and 600 cycles, between 5 and 400 cycles, between 5 and 200 cycles, between 5 and 100 cycles, or even between 5 and 50 cycles. The pipette tip may have an opening of between 20 gauge and 26 gauge, such as an opening between 20 gauge and 24 gauge, or even an opening between 20 gauge and 22 gauge. The resulting emulsion can include aqueous phase droplets having a major peak between 5 µm and 15 µm, such as a major peak between 5 µm and 12 µm, or even between 5 µm and 10 µm. A major peak is the highest peak within a multimodal distribution.

In an example, the emulsion can be distributed among tubes or wells over a thermocycling device. The temperature of the emulsion can be cycled to facilitate PCR or can be held at a constant temperature for RPA. As a result, particles within the emulsion droplets can be conjugated with copies of target polynucleotides.

The emulsion can be broken by applying emulsion breaking reagents to the emulsion. The emulsion may further be broken using a centrifuge apparatus. In an example, an emulsion breaking solution includes a surfactant in an aqueous solution. In another example, emulsion breaking solutions can include polymer species operable to facilitate phase separation. Such phase separation may be further encouraged by centrifugation. Once the emulsion is broken, the oil phase can be separated from the aqueous phase. The aqueous phase includes amplified particles that include multiple copies of target polynucleotides.

Optionally, the particle solution can be further enriched to remove particles that do not include copies of the target polynucleotides. In an example, particles that include copies of the polynucleotides can be coupled with magnetic particles. The solution including the particles coupled to the magnetic particles can be moved to a position adjacent a magnet. Those particles coupled to the magnetic particles can be secured within a tube adjacent to the magnet, while other particles not secured to the magnetic particles can be flushed or washed from the tube using a washing reagent solution. Following washing, the magnet can be moved or the tube can be moved from adjacent the magnet, releasing the magnetic particles. The particles coupled to the magnetic particles can be detached from contact with magnetic particles using chemical methods. The magnet can be used to secure the magnetic particles, which are not coupled to particles having copies of target polynucleotides. A solution including the particles having target polynucleotide copies can be removed and can be loaded onto a sequencing device, such as a chip including an array of sensors.

In an example, the solution including particles coupled to copies of the target polynucleotides can be applied over the array. The solution can be applied in a single aliquot or can be applied in partial aliquots followed by centrifugation. In an example, the array can be formed of a substrate that is placed within a tray on the centrifuge. Following each application of an aliquot of the solution including particles having copies of the target polynucleotides, the substrate can be centrifuged to facilitate deposition of the particles on the array. As a result, a loaded sensor array is provided from a sample including set of target polynucleotides without the intervention of human contact.

Figure 16:
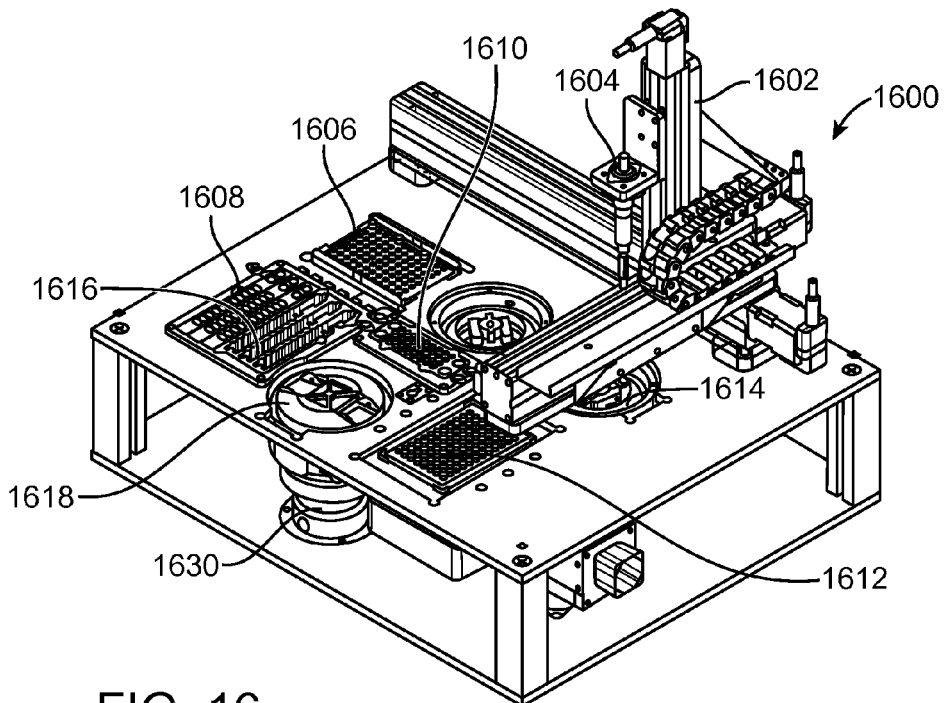
FIG. 16, FIG. 17, and FIG. 18 include illustrations of an exemplary sample preparation system.
Figure 17:
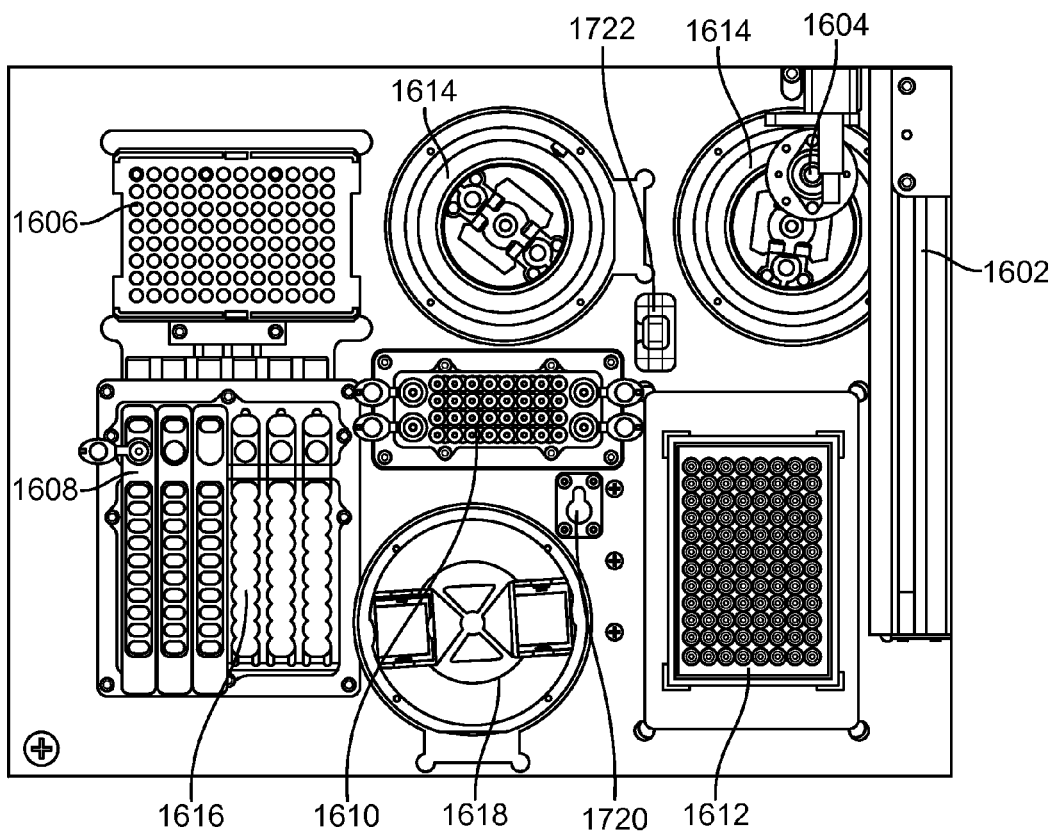
Figure 18:
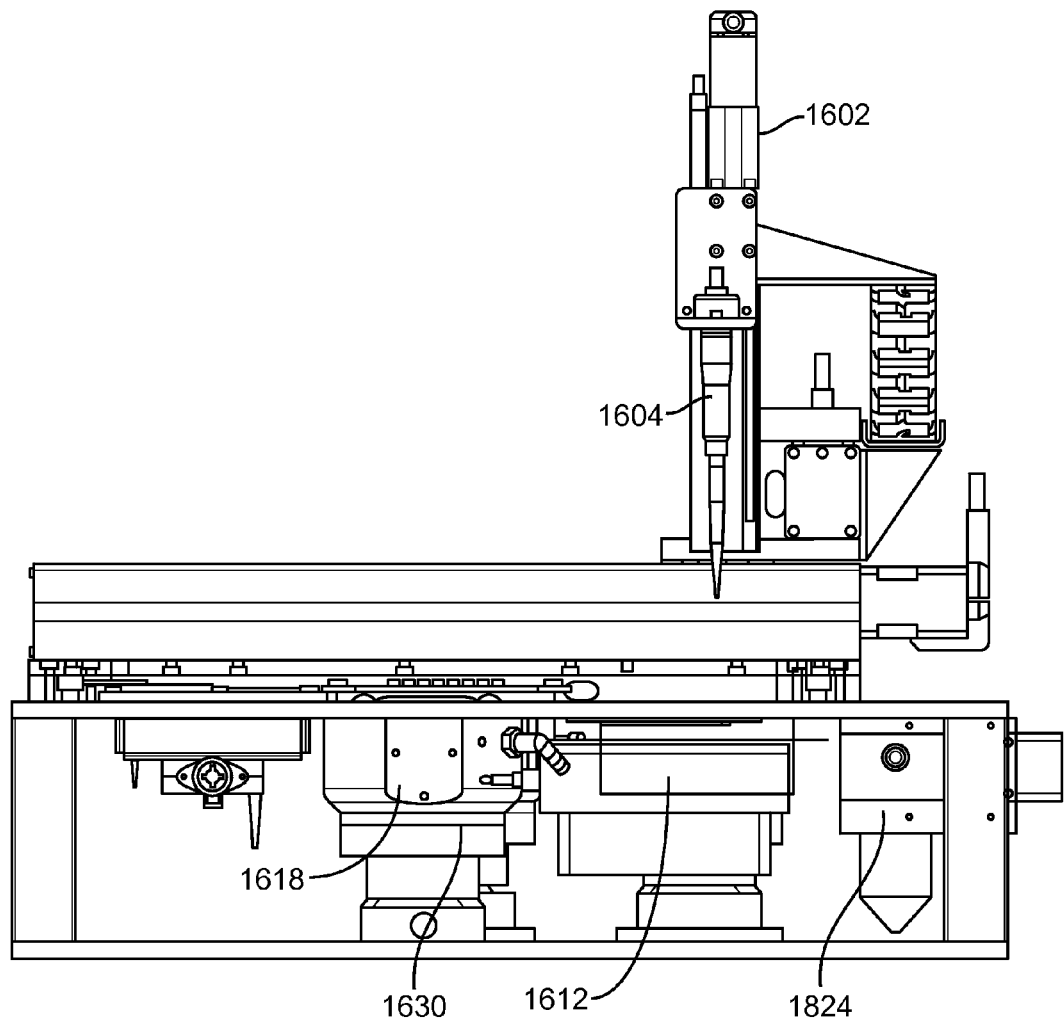
Figure 40:
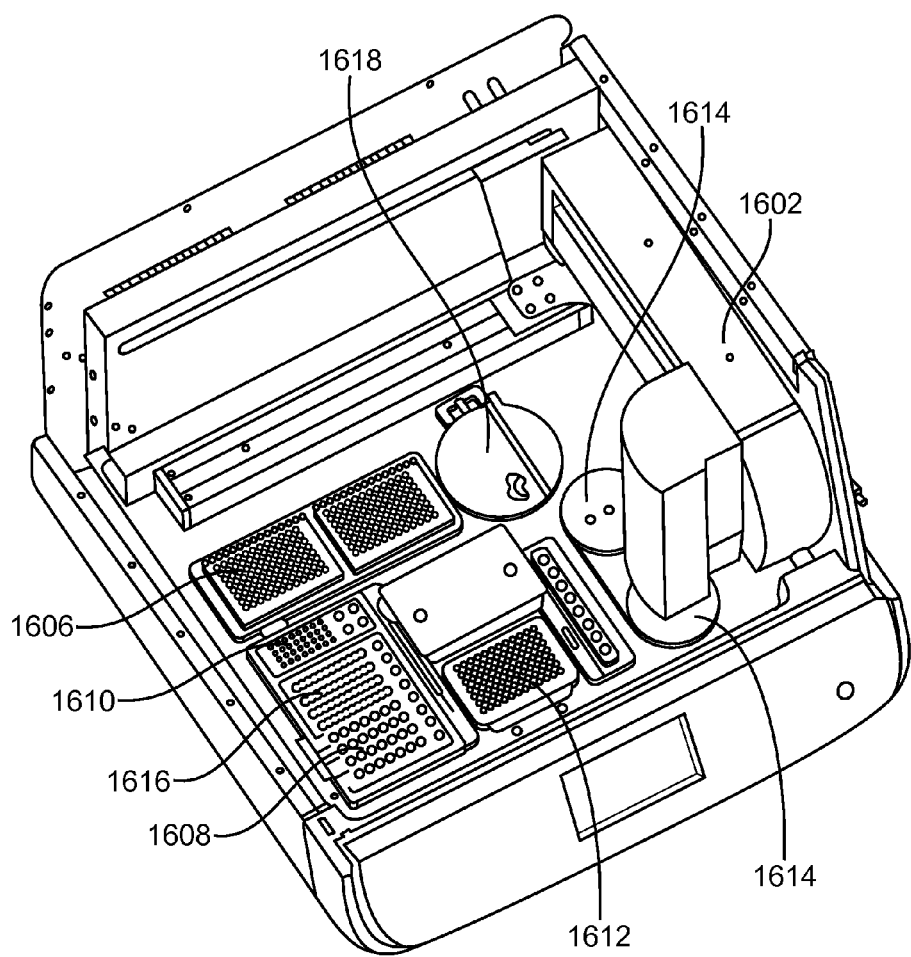
FIG. 40 includes an illustration of an exemplary sample preparation system.

In another embodiment, FIG. 16, FIG. 17, and FIG. 18 illustrated exemplary system for sample preparation and sequencing device loading. FIG. 40 illustrates an alternative configuration. The system 1600 includes a translation device, such as an xyz-robot 1602 operable to move a syringe pump 1604 over ranges of three orthogonal axes. The system 1600 further includes a tip rack 1606 for storing pipette tips useful by the syringe pump 1604. The system 1600 can also include a tube rack 1616 that can store empty tubes or can store strips of reagent tubes, such as reagent to strip 1608. In a further example, the system 1600 can include a chilled block 1610 for storing temperature sensitive reagents, such as enzymes. The system 1600 can further include a thermocycler 1612, one or more emulsion breaking centrifuges 1614, and a bead loading centrifuge 1618 with motor 1630. The system 1600 can further include an optical sensor 1722 or a tip removal device 1720.

In operation, the translation device 1602 manipulates the position of the syringe pump 1604 to retrieve tips from the tip rack 1606 and perform the various functions of the system 1600. For example, the syringe pump 1604 can be utilized along with reagents of the reagent rack 1616 to form an emulsion including enzymes and a sample in an aqueous discontinuous phase surrounded by an immiscible continuous phase. For example, the sample and enzyme solutions can be stored in the chilled reagent block 1610. The emulsion can be formed within a tube in the reagent rack 1616. In particular, the emulsion can be generated by rapid pipetting. In another example, the emulsion can be generated by pipetting through a restriction.

Following formation of the emulsion, the emulsion can be transferred to a thermocycler plate on a thermocycler 1612 using the translation device 1602 and the syringe pump 1604. The thermocycler plate 1612 can be utilized to perform polymerase chain reaction (PCR) or recombinase polymerase amplification (RPA). Upon completion of the PCR reaction, the emulsion can be transferred from the thermocycler 1612 to one of the emulsion breaking centrifuges 1614. The emulsion can be injected into the emulsion breaking centrifuge 1614 that includes tubes having a surfactant solution. As the centrifuge rotates, the emulsion is injected into the centrifuge. When the emulsion contacts the surfactant solution within the tubes of the centrifuge 1614, aqueous phase components are driven into the solution while oil phase components are removed from the tube.

The PCR or RPA process can generate amplified beads including a number of target polynucleotides. Such amplified beads can be washed and separated from other aqueous solution components using an enrichment system. In particular, the reagent rack 1616 can be modified with the magnet system to permit enrichment using magnetic particles that bind to the amplified beads.

Following enrichment, the beads can be transferred and loaded onto a sequencing device, such as a chip configured for detecting sequencing byproducts, using the loading centrifuge 1618. For example, aliquots of the solution including the amplified beads can be injected into ports on the sequencing device disposed on the rack within the loading centrifuge 1618. The centrifuge 1618 can be spun to facilitate the loading. The process can be repeated one or more times to improve loading density. As a result, a sequencing device loaded with amplified particles, incorporating amplified target nucleotides from the sample, is provided with minimal human interaction.

Throughout the process, the syringe pump 1614 can utilize a variety of pipette tips acquired from the pipette tip rack 1606. Further, tips can be provided that assist with movement of magnets, loading of tubes within the emulsion breaking centrifuge 1614, or other functions. To assist with removal of the tips from the syringe pump 1604, a tip removal device 1720 can be provided. A tip can be inserted into the larger diameter opening of the tip removal device 1720 and slid under a smaller diameter opening. When the syringe pump is moved in a vertical direction by the translation device 1602, the tip can be dislodged from the syringe pump 1604. Alternatively, a syringe pump 1604 can be selected that has an automated or built-in tip removal device.

Further, the system 1600 operates in an automated fashion relying on repeated capturing and removal of pipette tips, as well as reliable positioning of the pipette tips for performing various functions. The system 1600 can include an optical sensor 1722. The optical sensor 1722 can assist with determining whether a pipette tip has been secured to the syringe pump 1604 or whether a pipette tip has been successfully removed from the syringe pump 1604. In another example, the optical sensor 1722 can be utilized to calibrate movement of the syringe pump 1604 by the translation device 1602.

An emulsion breaking centrifuge 1614 may further utilize a vacuum system for collecting the oil phase once the emulsion is broken. As illustrated at FIG. 18, the system 1600 can further include a vacuum collection system 1824.

Figure 19:
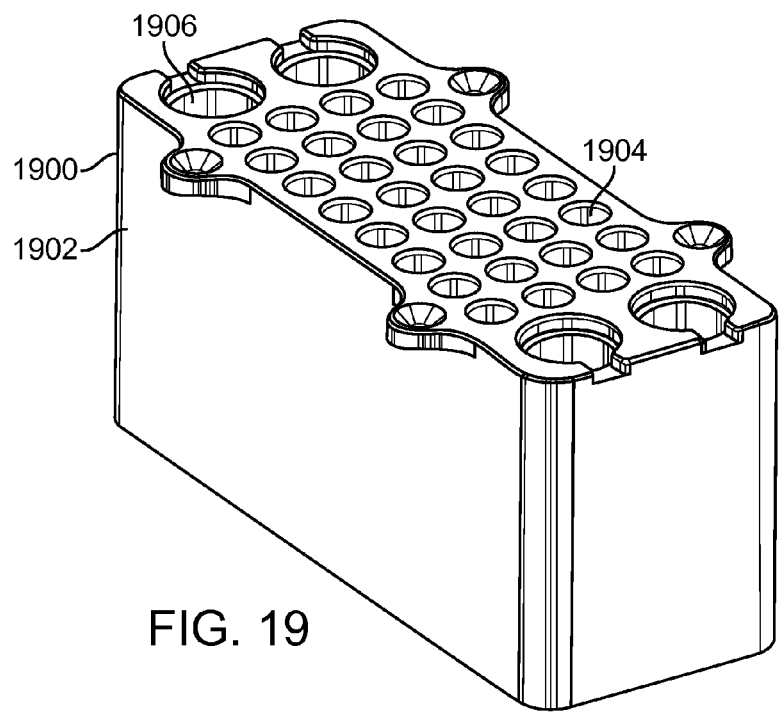
FIG. 19 includes an illustration of an exemplary reagent holder.

FIG. 19 illustrates an exemplary chilled reagent rack 1900, such as a chilled reagent rack 1610. The reagent rack 1900 can include a chilled body 1902 in which holes 1904 are provided to receive tubes of reagents. In addition, the system can include one or more holes 1906 for receiving tubes of a different diameter. The chilled block 1902 can be chilled using a fluid, such as ice chilled fluid. In another example, the chilled block 1902 can be cooled using a Peltier cooler. In particular, the chilled reagent rack 1900 can be used for storing sequencing polymerase, reagents, samples, an emulsion, or a combination thereof.

Figure 20:
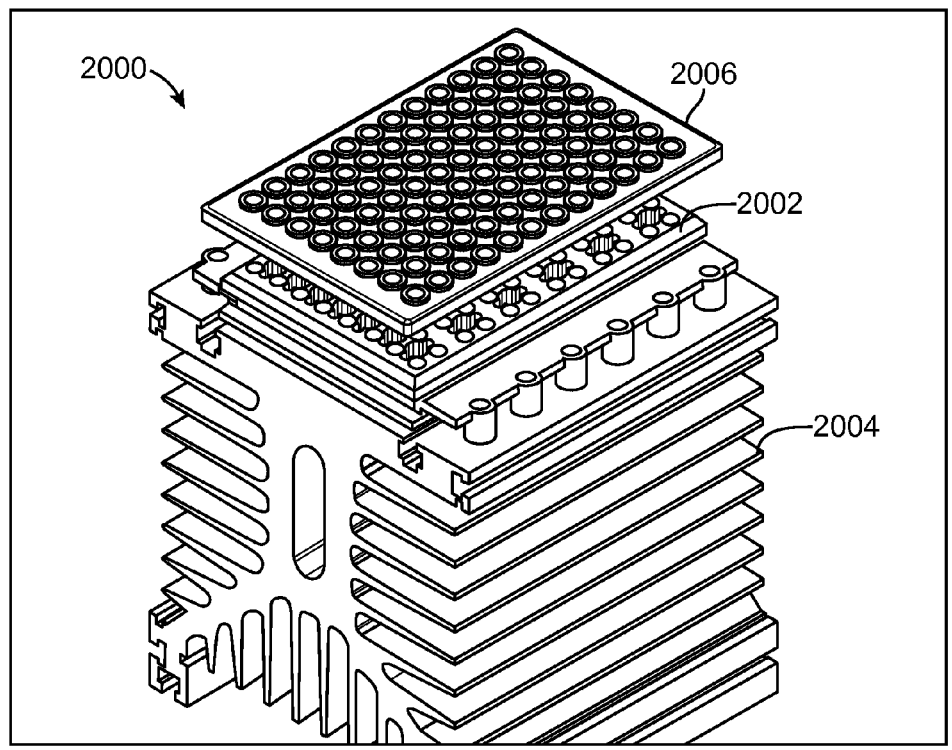
FIG. 20 includes an illustration of an exemplary PCR device.
Figure 21:
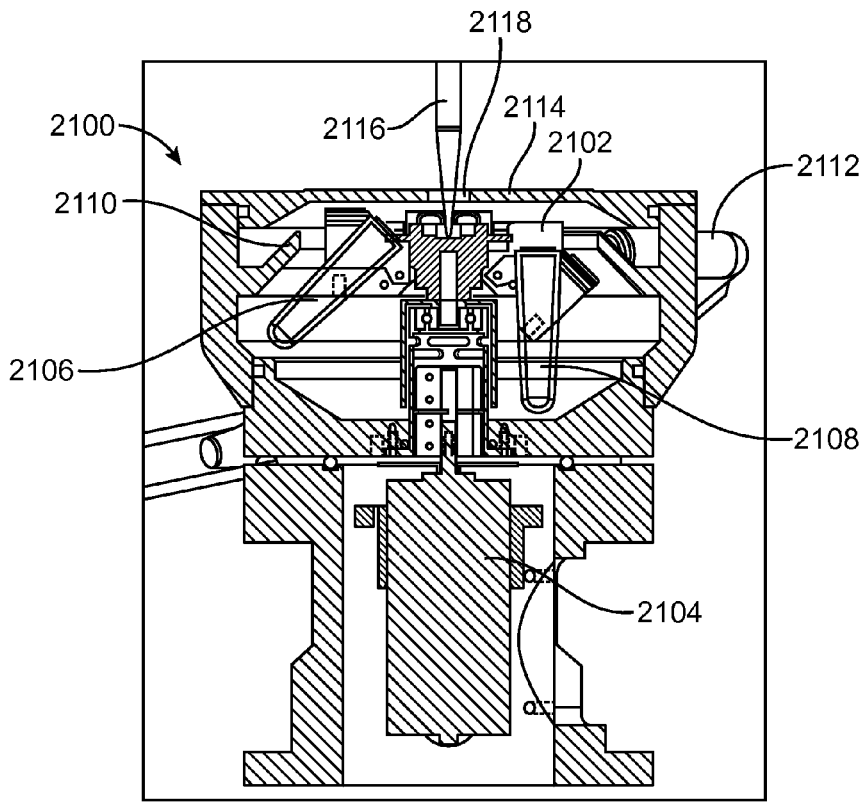
FIG. 21, FIG. 22.

As illustrated in FIG. 20, an exemplary thermocycler 2000 includes a thermal plate 2002 and a heatsink 2004. In a particular example, the thermal plate 2002 can utilize thermal electric chillers operated by various controlling electronics that cycle the temperature using thermal cycling algorithms. A thermal cycle plate 2006 can be applied over the thermal plate 2002 that cycles the temperature of the thermal cycle plate 2006 and dissipates waste heat into the heatsink 2004. Optionally, the thermocycler 2000 can include a mechanized lid to be moved into place over the thermal cycle plate 2006. The mechanized lid can be utilized to hold a thermal cycle plate 2006 against the thermal plate 2002, improving thermal contact between the thermal cycle plate 2006 and the thermal plate 2002. In another example, the mechanized lid can be utilized to isolate samples during PCR or RPA.

Once PCR or RPA is performed utilizing the thermal cycle system, emulsions can be broken using an emulsion breaking centrifuge. FIGS. 21-33 include illustrations of exemplary emulsion breaking centrifuges. An exemplary centrifuge 2100 includes a rotor 2102 coupled to a motor 2104. The rotor 2102 is configured to hold tubes 2106 and 2108 that change position based on the rotation of the rotor 2102. In particular, the rotor 2102 swings the tubes into position as illustrated by 2106 when in motion and permits the tubes to fall vertically into position as illustrated by 2108 when the rotor 2102 is stationary. When the rotor 2102 is rotating and the tubes are in the position as illustrated by 2106, an emulsion can be applied to the system, such as by using pipette 2116. The emulsion falls into a tube that includes a surfactant solution, breaking the emulsion and driving aqueous components along the length of the tube. Oil phase components can be slung from the tube and captured by a lip 2110. The slung oil can be captured by a vacuum system accessible through tube 2112.

Optionally, the centrifuge 2100 can include a lid 2114. The lid 2114 can be automated, lowering into place, or can be a permanently disposed lid 2114. The lid 2114 includes a centralized access to 2118 to permit a pipette tip to access the rotor 2102.

Figures 22, 23:
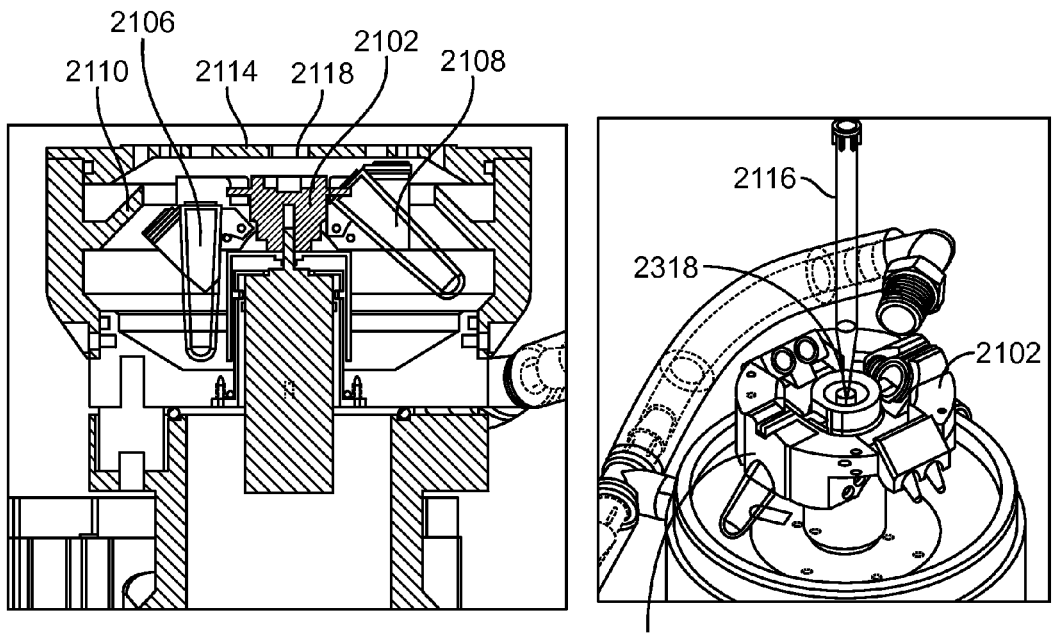
FIG. 23, FIG. 24, FIG. 25, FIG. 26, FIG. 27, FIG. 28, FIG. 29, FIG. 30, FIG. 31, FIG. 32, and FIG. 33 include illustrations of exemplary centrifuge devices.
Figure 24:
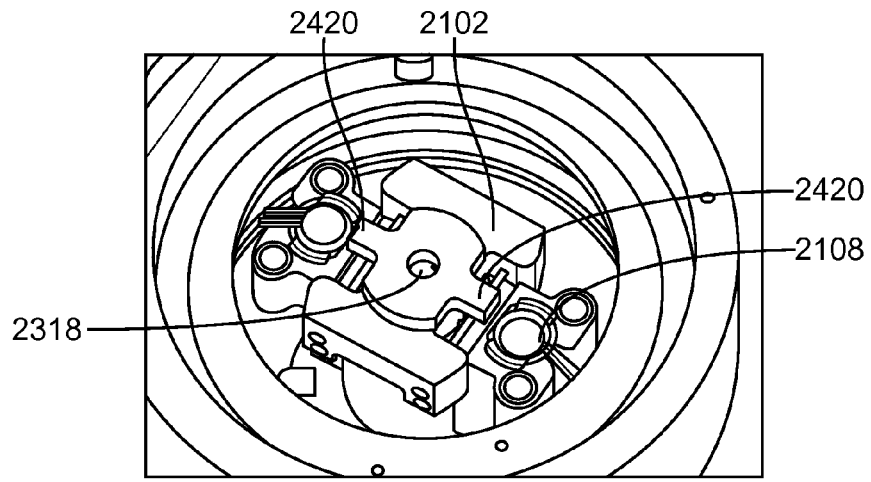
Figure 25:
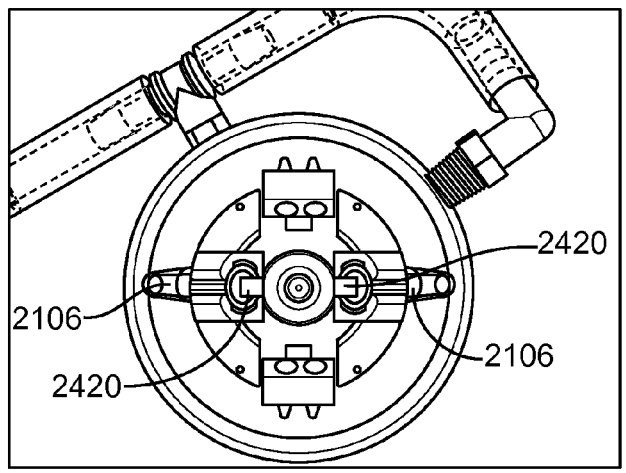
Figure 26:
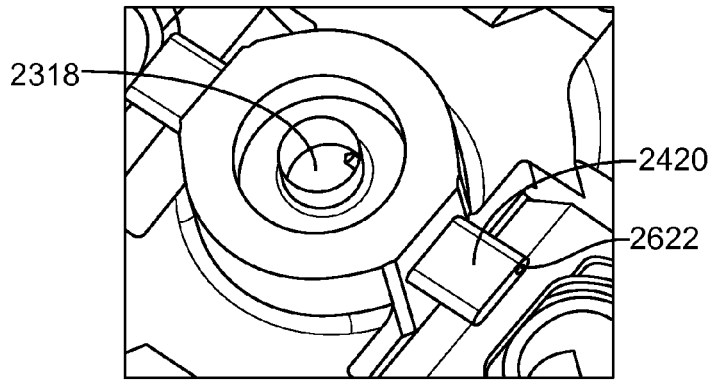
Figure 27:
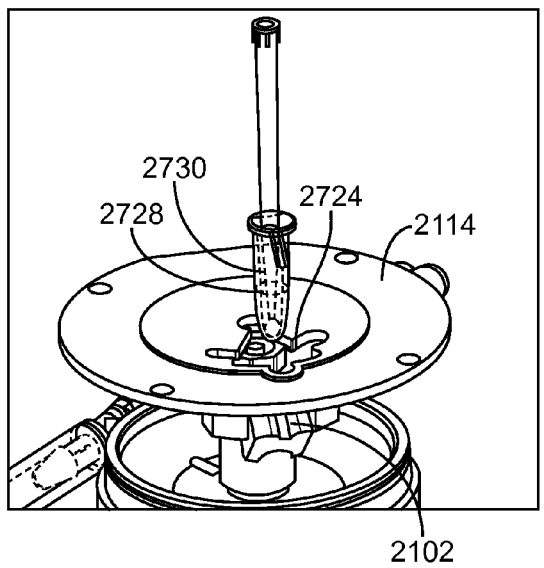
Figure 28:
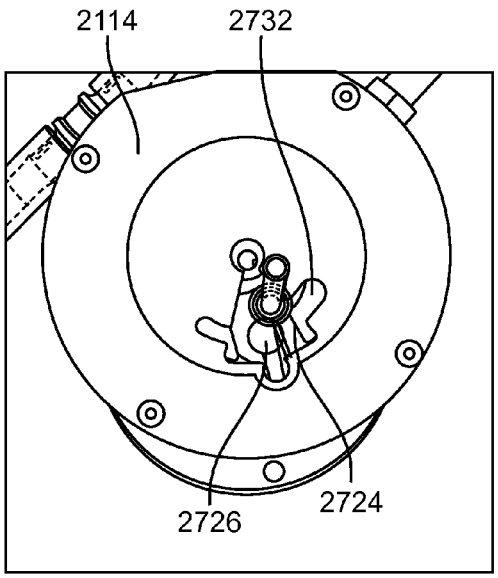
Figure 29:
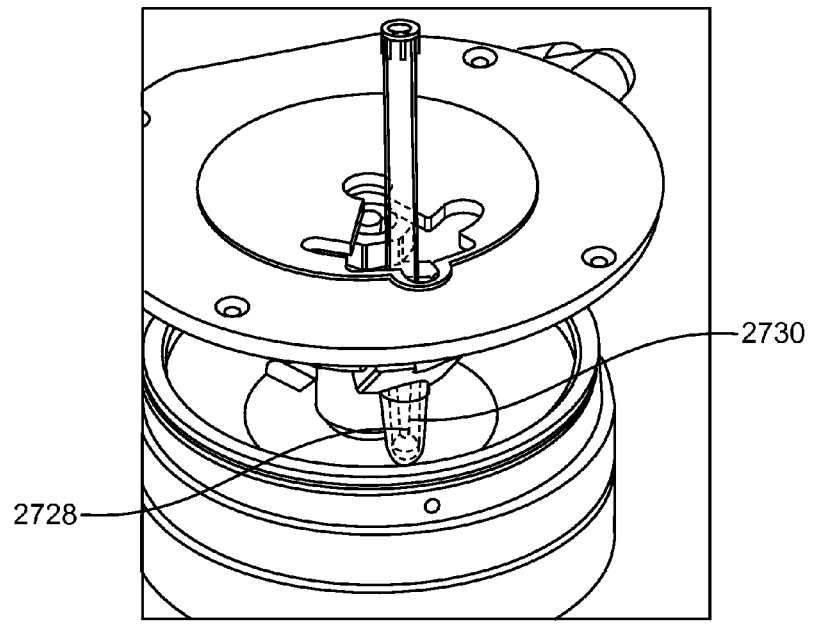

In an example, the pipette tip 2116 can provide an emulsion to a slinger 2318, as illustrated in FIG. 23. The slinger 2318 distributes the emulsion to one or both of the tubes. As illustrated in FIG. 24, the slinger includes arms 2420. When the rotor 2102 is not in motion, the tubes 2108 hang in a vertical position and can be accessed past the arm 2420 of the slinger 2318. However, as illustrated in FIG. 25, when the tubes swing up during rotation, the arm 2420 extends into the tubes, allowing any fluid applied into the cylinder 2318 to flow into the angled tubes 2106. In particular, the arm 2420 can include an effluent port 2622, as illustrated in FIG. 26. As emulsion is applied to the slinger 2318, emulsion exits the slinger 2318 through the effluent port 2622 into the tubes in an angled position during rotation of the rotor 2102.

In a particular example, the lid 2114 is a permanently applied lid secured to the system throughout operation. As illustrated in FIG. 26, FIG. 28, FIG. 29, FIG. 30, FIG. 31, FIG. 32 and FIG. 33, tubes can be inserted and removed from the centrifuge 2100 and the rotor 2102 using adapted pipette tips. For example, an adapted pipette tip 2730 can secure a tube 2728 for insertion into the rotor 2102. The lid 2114 can include an opening 2724 for inserting the tube when the opening is aligned with the rotor 2102. In an example, an opening 2726 in the rotor 2102 can receive the tube 2728 through the opening 2724 in the lid 2114. The opening 2724 includes a larger portion for receiving the tube and includes a restricted portion 2732 to capture the tube 2728 while allowing the adapted pipette tip 2730 to be removed, leaving the tube 2728 in the opening 2726 of the rotor 2102.

Figure 30:
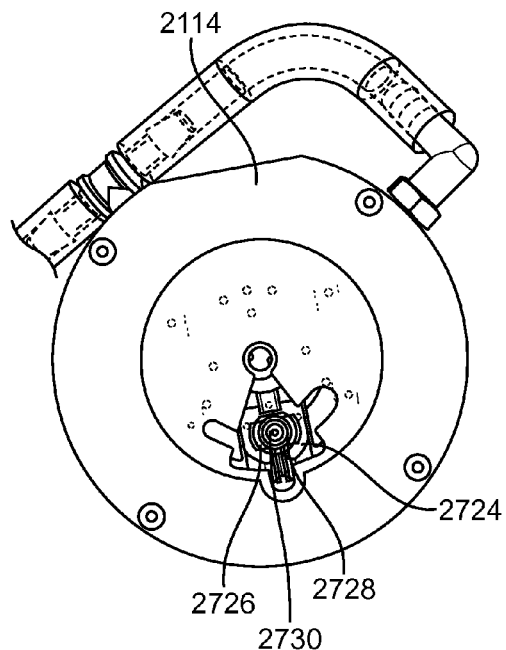
Figure 31:
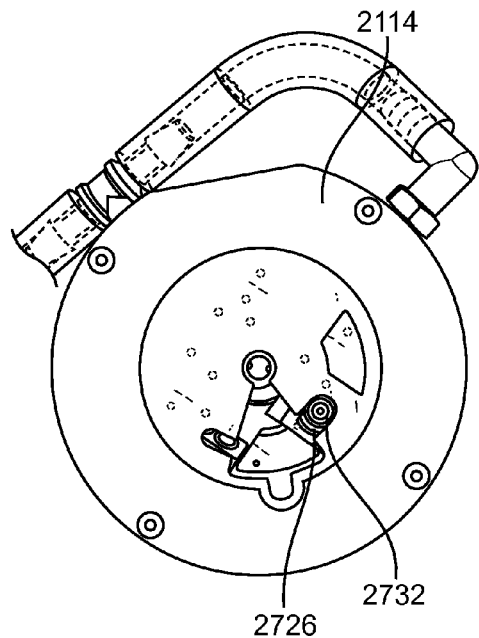
Figure 32:
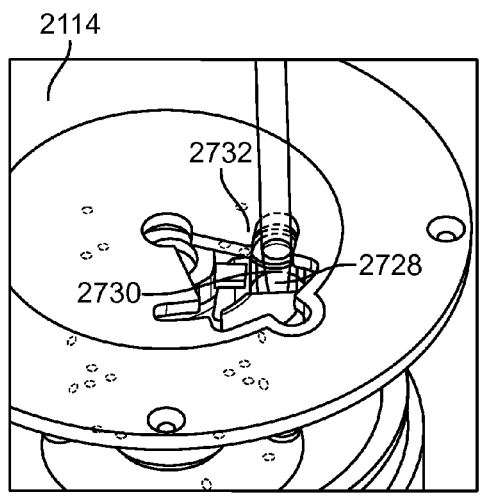
Figure 33:
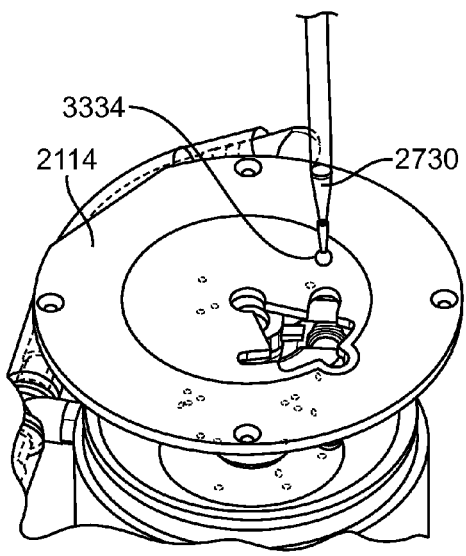

As illustrated in FIG. 30, the tube 2728 is applied through the opening 2726 when the rotor 2102 is positioned so that the opening 2726 is accessible through the larger portion of the opening 2724 in the lid 2114. The rotor 2102 and thereby the opening 2726 can be moved to a position adjacent a restricted portion 2732 of the opening 2724 in the lid 2114. As further illustrated in FIG. 32 and FIG. 33, the pipette tip 2730 can be withdrawn, leaving the tube 2728 in the rotor 2102. FIG. 33 further illustrates an exemplary adapted pipette tip 3334 for securing a tube. As illustrated, the adapted pipette tip 3334 includes a spherical portion that can be wedged within a conical section of the tube to remove the tube from the system or to apply the tube into the system. Alternatively, other designs can be utilized for securing a tube during transport to and from the centrifuge 2100.

Figure 34:
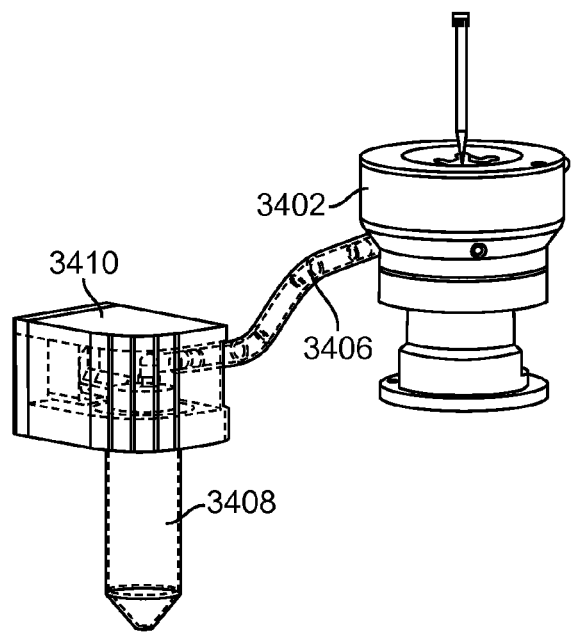
FIG. 34 and FIG. 35 include illustrations of exemplary vacuum collection systems.
Figure 35:
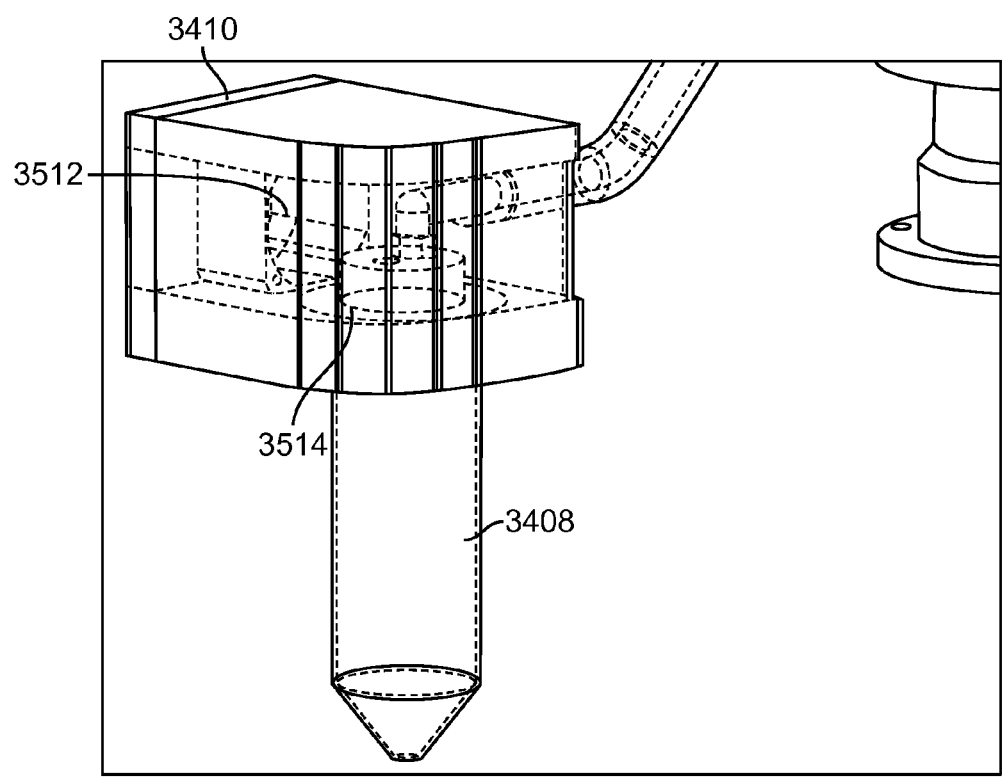

The centrifuge system is further attached to a vacuum system for receiving the immiscible phase, such as oil, following emulsion breaking. As illustrated in FIG. 34 and FIG. 35, a vacuum system can be coupled to a centrifuge 3402 with a tube 3406. The tube 3406 can include a portion that drains oil from an upper lip of the centrifuge 3402. In addition, the tube can include a portion that drains oil from a basin surrounding the rotor. Oil received into the tube 3406 flows into a receptacle 3408. A vacuum chamber 3410 is disposed over the receptacle 3408. In particular, an adapter 3514 receives oil via the tube 3406, depositing the oil into the receptor 3408 and drawing a vacuum through the adapter 3514 into the chamber 3410. The chamber includes a port 3512 for receiving a tube to a vacuum pump.

Figure 36:
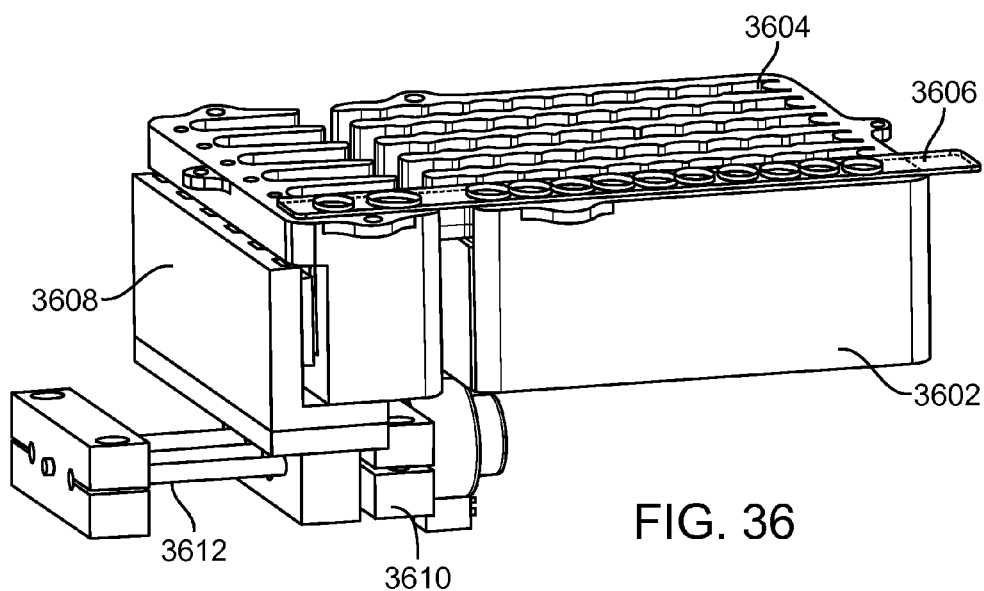
FIG. 36 includes an illustration of an exemplary enrichment system.

The system can further include a rack for storing reagents for holding tubes to be used in processes such as emulsion generation or enrichment. For example, as illustrated in FIG. 36, a rack 3602 includes opening 3604 configured to receive a tube strip 3606. In an example, the tube strip 3606 can store reagents. In another example, the tube strip 3606 can include empty tubes for performing various functions, such as washing or enrichment.

When used in an enrichment system, the reagent tube holder 3602 may further include a magnetic system useful as part of an enrichment process that utilizes magnetic particles. For example, the magnetic system can include a movable magnetic plate 3608 secured to a rail system 3612 and movable back and forth along the rail system 3612 via a screw device 3610. While the screw device 3610 is illustrated, other systems such as pneumatic devices, spring enabled devices, or other mechanisms can be utilized to move the magnetic plate 36082 to and away from the reagent holder 3602. While a magnetic plate is shown as applying a magnet to the side of the tube. Alternatively, the magnet can be applied to the bottom of the tube.

Optionally, the reagent to holder 3602 can be a thermal controlled reagent tube holder, such as including heater. In particular, heated reagent tube holder can assist with melt off and other functions.

Figure 37:
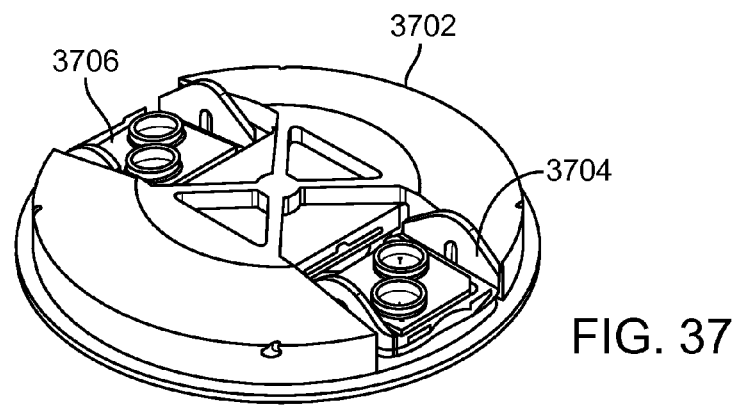
FIG. 37 and FIG. 38 include illustrations of exemplary sequencing device loading devices.
Figure 38:
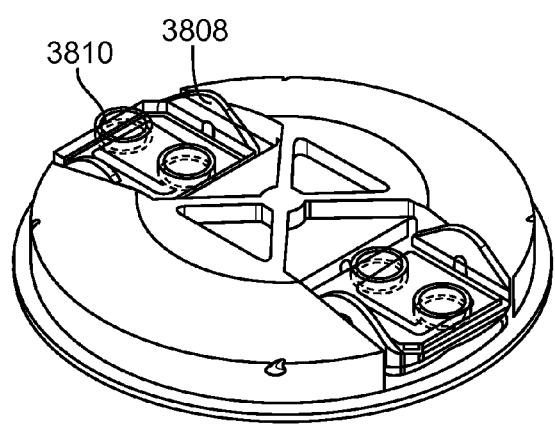

The system can also include a loading centrifuge. For example, as illustrated in FIG. 37 and FIG. 38, buckets 3704 can be configured to hold sequencing devices 3706, such as sequencing chips, and are secured to a rotor 3702 of the bead loading centrifuge. As illustrated in FIG. 38, the orientation of the openings of the chip 3810 can be manipulated by changing the configuration of the bucket 3808. Alternatively, the buckets can be configured to hold several different chip configurations. Features on the rotor can prevent inward swinging of the bucket and sequencing device. Alternatively, features on the rotor can permit an outward swing of the buckets to varying angles from vertical to less than vertical.

Figure 39:
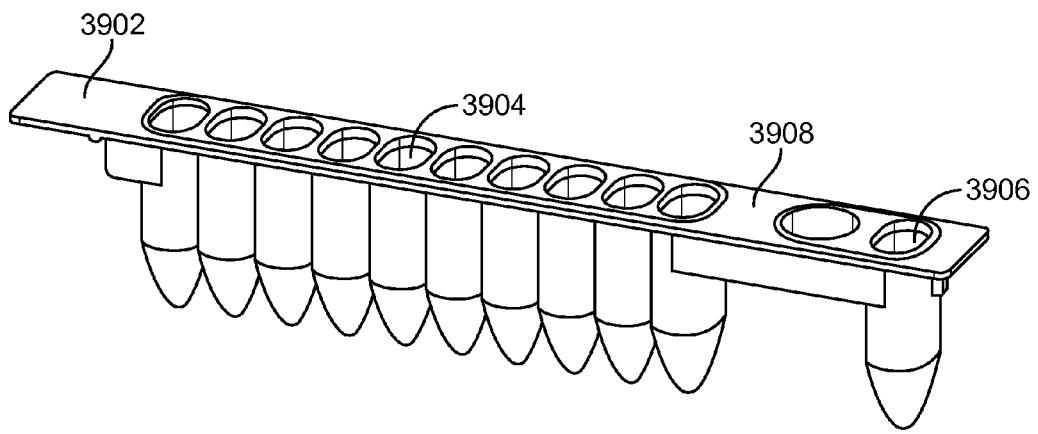
FIG. 39 includes an illustration of an exemplary reagent strip.

Optionally, the system can be further simplified by utilizing reagent cartridges. The reagent cartridge can be configured to fit within the reagent holder. In an example, the cartridge can be provided for forming the emulsion or can include wash solutions. In another example, the cartridge can be configured for performing the enrichment function. A further cartridge can be included that stores surfactant solutions for applying to the emulsion breaking centrifuge. Optionally, such cartridges can be prefilled and foil sealed so that the such cartridges can be dropped into the device with little further interaction with the user. In a particular example, a cartridge illustrated in FIG. 39 includes a strip 3902 in which tubes 3904 are formed. The strip can include a further tube 3906 separated from a set of tubes 3904 by a strip extension 3908.

In practice, the workflow can include preparing a master mix. For example, water, an amplification mixture, enzymes, a library, and conjugated particles are transferred to a tube and mixed. Such a reagents can be stored either on the reagent rack 1616 or on the chilled reagent rack 1610, as illustrated in FIG. 17.

An emulsion can be formed. For example, an immiscible liquid, such as an oil, can be transferred to an emulsification tube. The master mix can also be transferred to the emulsification tube and an emulsion can be formed by repeatedly aspirating and depositing the mixture. Once formed, the emulsion can be transferred to a PCR plate disposed on the thermocycler 1612. Optionally, emulsification and plating can be performed more than once.

The process can further include amplification to amplify a sample library onto the conjugated particles. For example, an oil can be applied over each of the wells of the PCR plate in which an emulsion is disposed. Optionally, a physical lid can be applied over the PCR plate. The thermocycler 1612 can thermal cycle to perform PCR. Following PCR, the oil can be aspirated from the top of each well.

The process can further include breaking and washing the emulsion. For example, the system can fill rotor tubes with a recovery solution, such as a surfactant solution. The rotor tubes are housed within the emulsion breaking centrifuge. The centrifuge can be spun and additional recovery solution can be applied to a slinger at the top of the rotor. Once the centrifuge reaches the desired rotation speed, the tubes can be topped off with recovery solution by applying recovery solution to the slinger.

The amplified emulsion can be drawn from wells of the PCR plate and dispensed into the slinger. As the emulsion is retrieved from each of the wells of the PCR plate and applied into the centrifuge, the amplified particles can form a pellet at the bottom of the rotor tube. Additional recovery solution can be applied to the slinger. In addition, wash solution can be applied to the slinger. The centrifuge can be stopped. Optionally, some of the recovery solution can be removed and the beads can be re-suspended. Once the amplified particles have been re-suspended, the particles can be removed from the centrifuge.

Further, the amplified particles can be enriched. For example, magnetic beads can be washed by applying a magnet to a tube in proximity to the magnetic beads, securing the magnetic beads to a wall of the tube. The amplified particles derived from the emulsion breaking centrifuge can be applied to the magnetic beads. The magnet can be moved away from the system and the amplified particles mixed with the magnetic beads to capture the amplified particles on the magnetic beads. The amplified particles attached magnetic beads can be captured using the magnet and the solution can be washed with a wash solution. The magnet can be removed and a tube refilled with wash solution. The process can be repeated several times to wash particles that were not amplified and to remove other contaminants from the system. A denaturant can be added to separate magnetic particles from the amplified particles. The magnetic particles can be captured with the magnet and the amplified particles can be transferred to a different tube.

Optionally, the amplified particles can be further washed by applying the particles into the emulsion breaking centrifuge tube, spinning the amplified particles, and carefully remove the wash solution. The enriched amplified particles can be re-suspended.

In preparation for sequencing, primers can be added into the particles. The particles can be transferred to the thermal block, hybridizing primers to the target polynucleotides on the amplified particles. Polymerase can also be added.

A sequencing device disposed on the loading centrifuge 1616 can be flushed with a wetting agent. Extra wetting agent can be collected from the sequencing device. The sequencing device can be further flushed with an annealing buffer and excess annealing buffer can be collected and discarded. Aliquots of the amplified particles prepared for sequencing can be transferred to the sequencing device using various combinations of transferring aliquots, removing excess aliquot and centrifuging.

In an embodiment, a system includes a syringe pump to couple to a pipette tip, a translation device to move the pipette tip, an enrichment device, and a centrifuge device. The enrichment device includes a mixing tube and a magnetic device movable relative to the mixing tube. The centrifuge device includes a rotor and a bucket to secure a sequencing device. The translation device is to position the pipette tip proximal to the mixing tube and proximal to the sequencing device.

Figure 41:
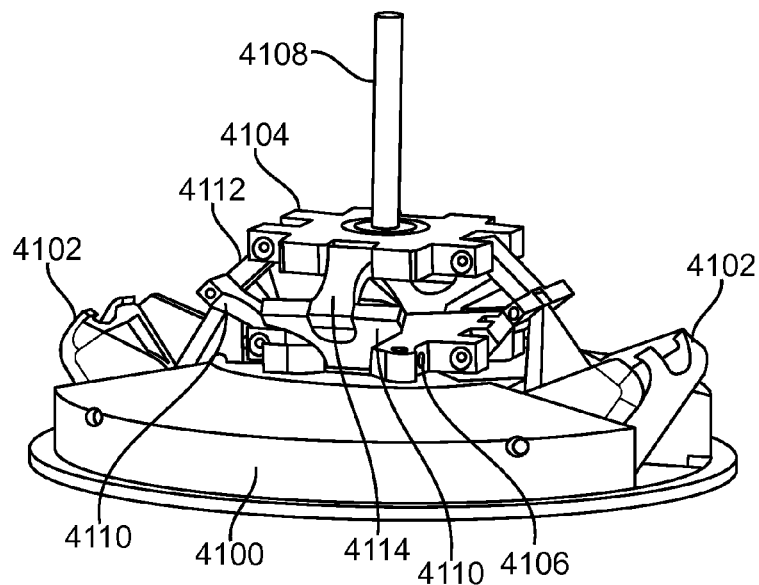
FIG. 41, FIG. 42, and FIG. 43 include illustrations of exemplary centrifuge rotors.
Figure 42:
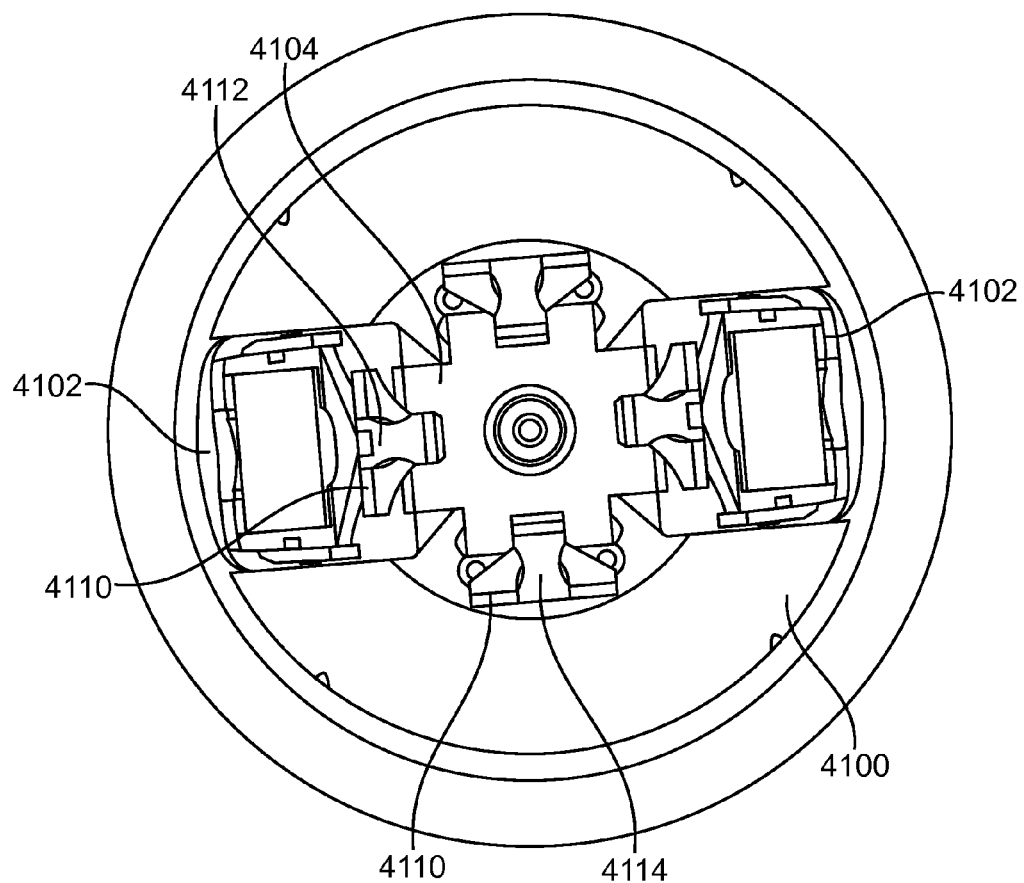
Figure 43:
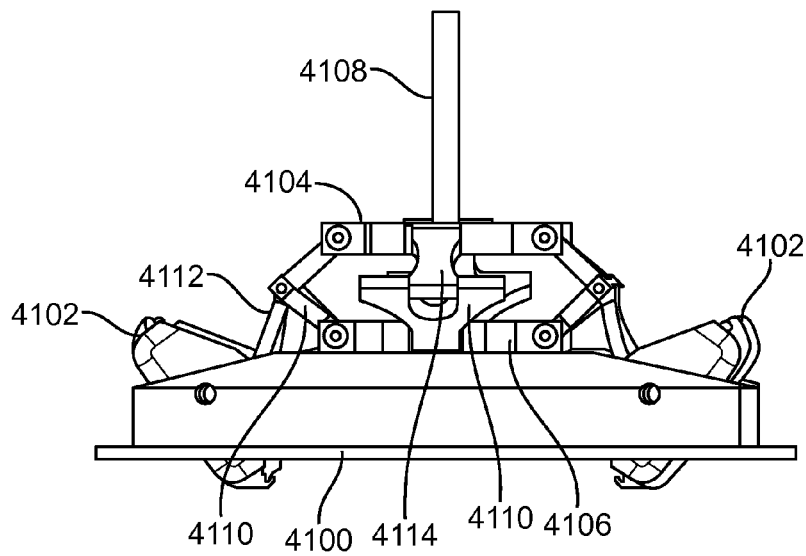

In another embodiment, an apparatus includes a motor, a rotor, and a bucket attached to the rotor and configured to receive a sequencing device. In example, FIG. 41, FIG. 42, and FIG. 43 illustrate an exemplary rotor 4100 to attach to a centrifuge motor to load beads onto a sequencing device. The rotor 4100 includes at least two buckets 4102 that can be moved from a horizontal position parallel to the plane of the rotation of the rotor 4100 to positions approximately perpendicular to the plane of rotation of the rotor 4100, or even positions upside down and close to parallel to the plane of rotation of the rotor 4100.

In the illustrated example, when an upper plate 4104 is motivated relative to a lower plate 4106, lever arms 4112 manipulate the position of the buckets 4102. For example, the upper plate 4104 can be motivated by an actuator attached abroad 4108. The actuator can be a linear actuator, a screw actuator, or any combination thereof. In particular, lower arms 4110 are pivotally coupled to the lower plate 4106 and are pivotally coupled to a lever arm 4112 or an upper arm 4114 at an end opposite to the end to which the lower arms 4110 are coupled to the lower plate 4106. The upper arm 4114 is pivotally coupled to the upper plate 4104 at a location opposite to the upper arm's attachment to the lower arm 4110. The lever arm 4112 is pivotally coupled to the upper plate 4104 at end opposite to which it is coupled to the bucket 4102. The lower arm 4110 can be coupled to the lever arm 4112 at a position between the coupling at the upper plate 4104 and a coupling at the bucket 4102.

When the upper plate 4104 is moved away from the lower plate 4106, the lower arms 4110 are drawn inward, towards an axis of rotation of the rotor 4100. As a result, the lever arm 4112 is moved into a more vertical position and the buckets 4102 are moved into a horizontal position. When the upper plate 4104 is moved towards the lower plate 4106, the lower arm 4110 is motivated outward away from an axis of rotation of the rotor 4100, causing the lever arm 4112 to move to more horizontal position, raising the bucket 4102 into position angled away from horizontal. While the illustrated examples of FIG. 41 FIG. 42 and FIG. 43 illustrate a two bucket system, the system may be adapted to include four buckets, six buckets or more.

In use, a sequencing device, such as a sequencing chip with a flow cell, can be placed within the rotor bucket 4102. An aliquot of a solution including amplified beads can be placed within a flow cell of the sequencing device. The rotor 4100 can be rotated and the upper plate 4104 manipulated to position the bucket 4102 and thus, the sequencing device in a position horizontal or otherwise to facilitate loading beads within wells of the sequencing device. In an example, the buckets 4102 can take approximately horizontal positions or can be moved back and forth between positions of less than or greater than 90° as part of a process to move the solution including beads back-and-forth across the surface of the sequencing device.

Figure 44:
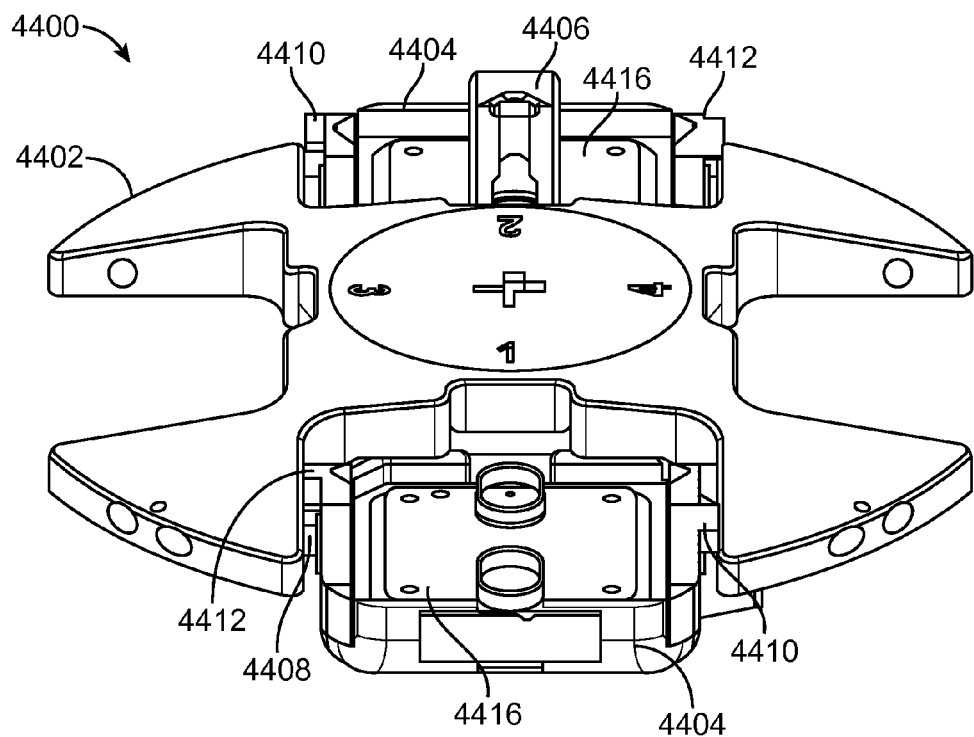
FIGS. 44-46 include illustrations of an exemplary centrifuge rotor.
Figure 45:
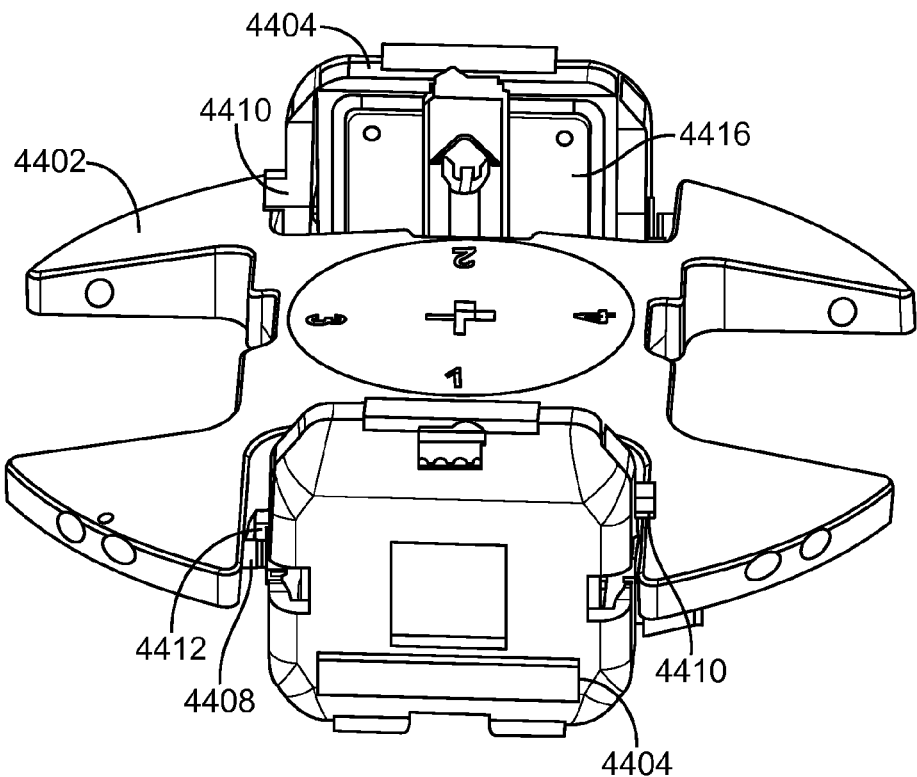
Figure 46:
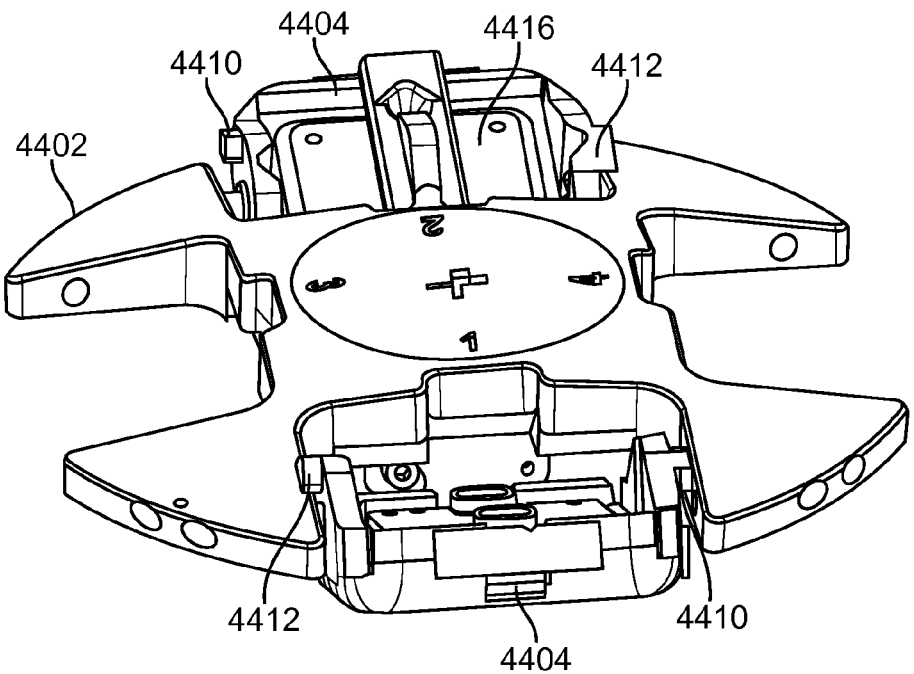

In an alternative example, an angle at which a chip bucket and chip are held during centrifugation can be manipulated using a weighted bucket and direction-based stops. For example, FIG. 44, FIG. 45, and FIG. 46 illustrate an exemplary rotor 4400 including a rotor plate 4402 connected to buckets or carriers 4404 by an axle 4408. The axle 4408 can extend across the recess in the rotor plate 4402 or can extend partly across the recess. In a further example, an axle 4408 is formed by two cylindrical extensions from the rotor plate 4402 into the recess. The bucket or carrier 4404 is slidably attached to the axle 4408 and can slide along the axle 4408 depending on the direction of movement of the rotor 4402. In addition, the carrier or bucket 4404 can rotate around the axle 4408. In particular, the bucket or carrier 4404 is weighted so that when the rotor plate 4402 is spending, the bucket or carrier 4404 rotates around the axis 4408 towards a position that is perpendicular to a plane of rotation of the rotor plate 4402.

The bucket or carrier 4404 can be configured to accept an electronic device 4416, such as a sequencing device. The electronic device 4416 can optionally be secured in the carrier or bucket 4404 by a clip 4406. The carrier or bucket 4404 can further include positional tabs or stops 4410 and 4412. The positional tabs 4410 and 4412 act to limit the amount of rotation around the axle 4408 depending on a direction of rotation of the rotor plate 4402. For example, as illustrated in FIG. 45, when the rotor plate 4402 spins clockwise, the buckets or carriers 4404 slide along the axle 4408 in a counterclockwise direction. The tab 4410 can engage the rotor plate 4402 setting a position of the bucket or carrier 4404 and limiting its rotation about the axle 4408 relative to the plane of the rotation. The positional tab 4412 is configured such that when the bucket or carrier 4404 slides along the axle 4408 in the counterclockwise direction, the positional tab 4412 does not engage the rotor plate 4402.

In another example illustrated in FIG. 46, the rotor 4402 rotates in a counterclockwise direction. The carrier or bucket 4404 slides along the axle 4408 in a clockwise direction. The positional tab 4412 engages the rotor plate 4402 limiting the amount of rotation of the bucket or carrier 4404 around the axle 4408. The positional tab 4410 is free to rotate and does not engage the rotor plate 4402. As such, the angle at which a chip or electronic device sits within the bucket during centrifugation is set by the position of the positional tabs 4410 and 4412 and the direction rotation of the rotor plate 4402.

In an example, the carrier 4404 rotates to a first angle when the rotor spins in one direction and a second angle with the rotor spins in a second direction. The first angle can be in a range of 70° to 110° relative to the plane in which the rotor spins. For example, the first angle is in a range of 80° to 95° relative to the plane. In a further example, the second angle is in a range of 20° to 65° relative to the plane. For example, the second angle is in a range of 35° to 50° relative to the plane.

Figure 47:
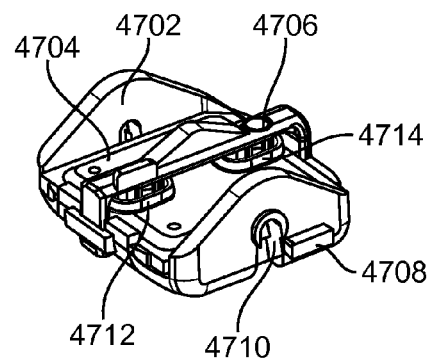
FIG. 47 includes an illustration of exemplary carrier bucket.

FIG. 47 includes an illustration of exemplary carrier or bucket 4702. The carrier or bucket 4702 can engage an axle at 4710. In addition, the bucket or carrier 4702 can be configured to receive an electronic device 4704, such as a sequencing device. The electronic device 4704 can include fluid ports 4712 or 4714. A clip 4706 can engage the electronic device 4704 to secure the electronic device 4704 to the carrier 4702. In particular, the clip 4706 can include portions to engage the fluid ports 4712 or 4714 of the electronic device 4704. The bucket or carrier 4702 includes positional tabs, such as tab 4708, that limit the rotation of the bucket or carrier 4702 relative to a plane of rotation of the centrifuge based on a direction of rotation.

Figure 48:
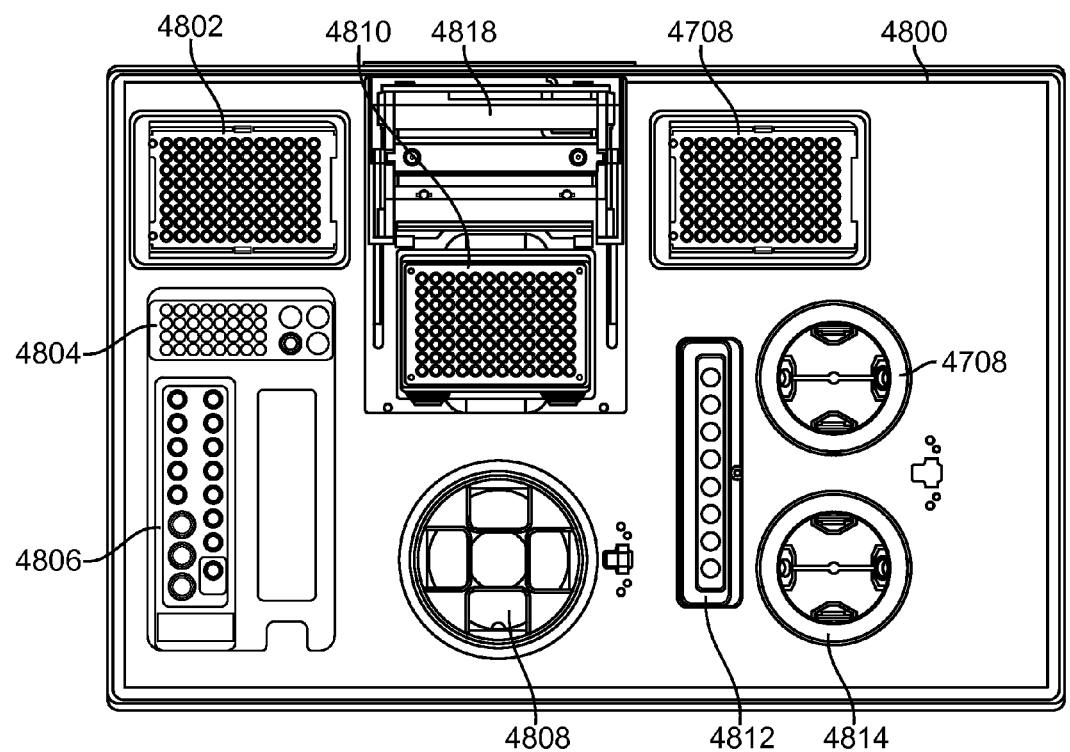
FIG. 48 includes an illustration of exemplary arrangement of devices.

In a further exemplary embodiment, FIG. 48 illustrates an exemplary arrangement of components for use in the system 4800. For example, the system 4800 can include a clean tip rack 4802, a chiller block 4804, and a reagent block 4806. Optionally, the chiller block 4804 and the reagent block 4806 can be temperature controlled.

In addition, the system can include a thermocycler 4810. The thermocycler 4810 can cycle the temperature of an emulsion or solution. Alternatively, the thermocycler 4810 can be held at a constant temperature for a period of time. The thermocycler can include a lid 4818 that can clamp over the thermocycler during operation.

In addition, the system 4800 includes a chip loading centrifuge 4808 that includes a rotor and bucket to receive electronic devices. The system 4800 can also include one or more centrifuges 4814. In particular, the centrifuges 4814 can be useful for breaking emulsions and for washing solutions. Optionally, the centrifuges 4808 or 4814 can include lids that lie over the centrifuges when in operation.

The system 4800 can also include and enrichment module 4812. In particular, the enrichment module 4812 includes a magnetic device to facilitate enrichment using magnetic particles. The system 4800 can also include used tip rack 4816.

Figure 49:
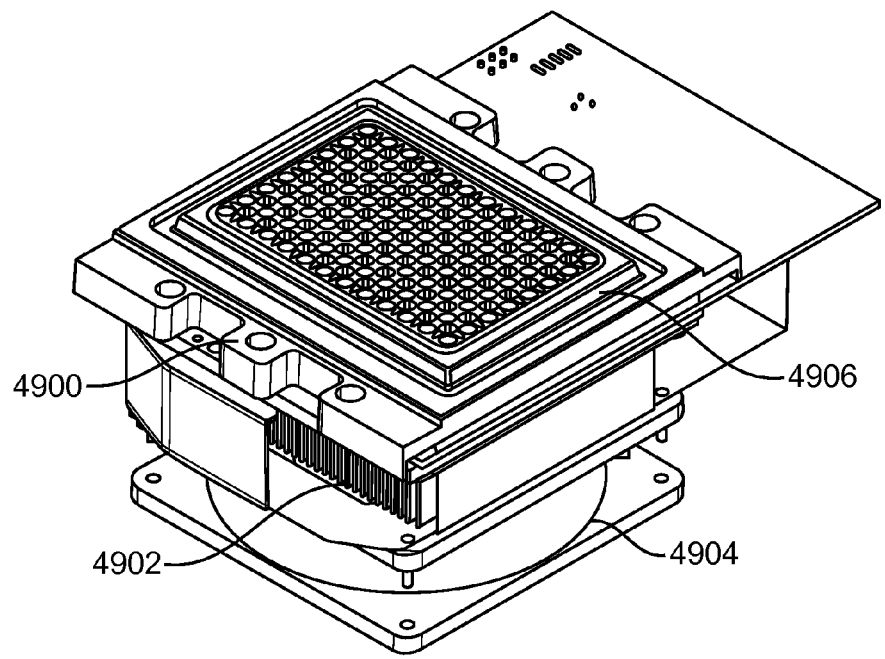
FIG. 49 includes an illustration of exemplary thermocycler.

FIG. 49 includes an illustration of an exemplary thermocycler 4900. The thermocycler 4900 includes a tray 4906 on which a multiwell plate, a set of tubes, or another thermal plate can reside. Temperature can be driven using Peltier devices. The thermocycler can also include a heat sink 4902 and a fan 4904.

Figure 50:
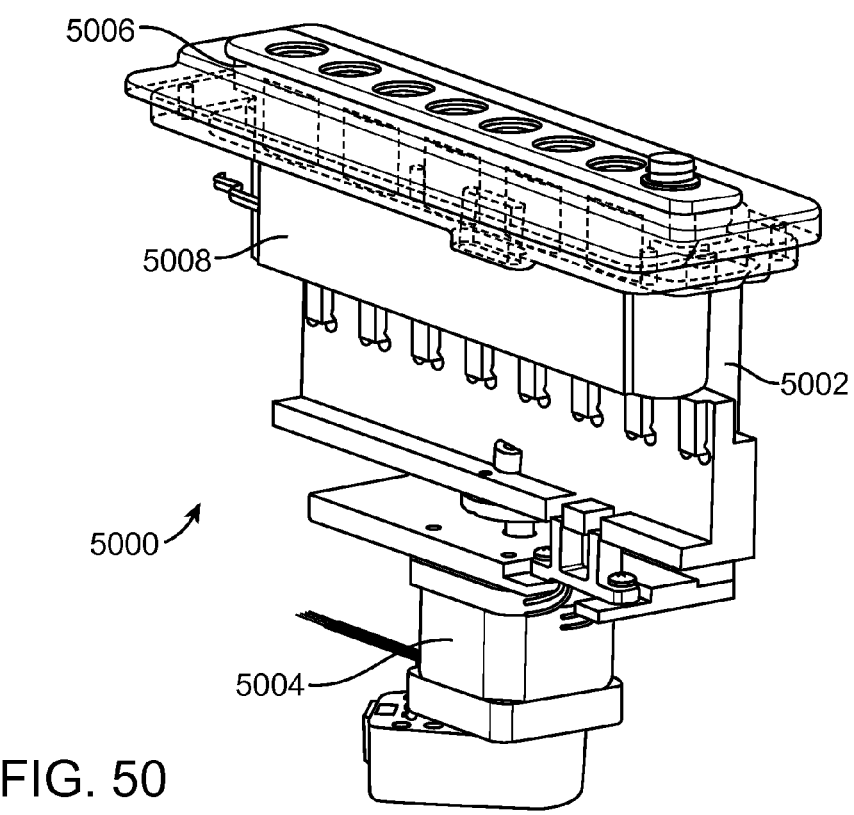
FIG. 50 includes an illustration of exemplary magnet system for use in an enrichment process.

FIG. 50 includes an illustration of exemplary enrichment module 5000. The enrichment module 5000 can include a magnetic plate 5002 that can be moved into position relative to tubes within a stand 5006 by an automated mechanism 5004. When in position, a magnetic field can be established through between 3 and 8 tubes. In addition, the enrichment module 5000 can include a heater 5008. In practice, solutions can be placed in the stand or in tubes in the stand 5006. Heat can be applied using the heater 5008 or a magnetic field may be positioned adjacent the tubes using the mechanism 5004.

Figure 51:
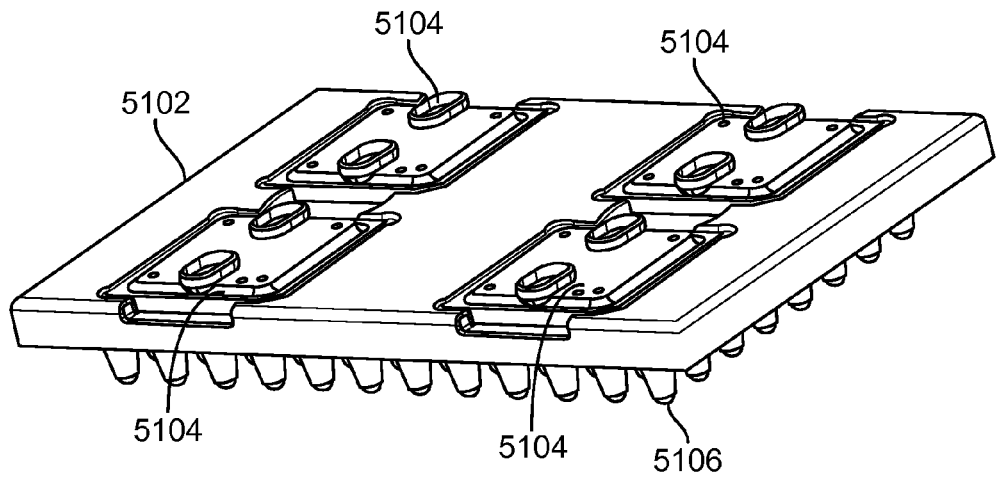
FIG. 51 includes an illustration of an exemplary thermal plate adapted to receive electronic components.

FIG. 51 includes an illustration of an alternative plate for use with the thermocycler. For example, the plate 5102 can be configured to receive electronic devices 5104, such as sequencing devices. In an example, the plate includes a patterned surface 5106 that mimic tubes to improve contact the thermocycler. Using the pipetting system, solutions can be applied and withdrawn from the electronic devices 5104. The temperature of the electronic devices 5104 can be controlled and optionally cycled using the thermocycler apparatus. Such a plate can be used for on-chip PCR or RPA. In such an example, the amplification solutions described above are applied directly to the sequencing device, optionally without beads. The temperature of the sequencing device is controlled to facilitate PCR or RPA. The sequencing device can then be washed and prepared for use in a sequencing system.

Figure 52:
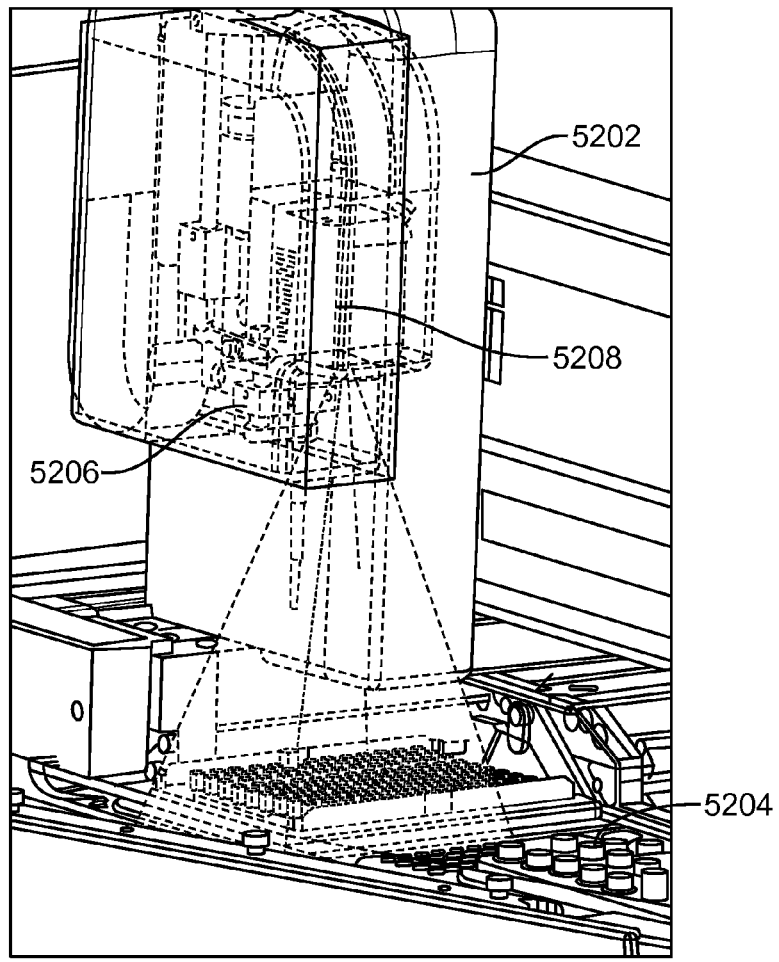

As illustrated in FIG. 52, the track system 5202 provides three-dimensional movement to position the end of a pipetting system 5206, which aspirates and deposit solutions as directed. The system further includes a deck 5204 with mounts and devices to store tips, tubes, and reagents for use in carrying out functions of the system. In addition, a camera system 5208 can be mounted adjacent the pipetting system 5206. The camera 5208 can form part of a vision system useful for calibrating and controlling movement of the track system 5202, perform a load check for consumables disposed on the deck 5204, and check for proper attachment or detachment of tips to the pipetting system 5206.

In an example, the system can use the camera 5208 to check that consumables have been properly loaded for use during operation of the system. For example, the camera 5208 can image a rack or device. The system can analyze the image, for example, identifying features within the image such as the circular features of a tube or tip. In an example, the image may be filtered and features within the filtered image analyzed. In particular, a string of Boolean values indicating the presence or absence of a tube or tip can be provided in an order based on an array of addresses. The string of Boolean values can be provided to a processor and the processor can determine whether consumables have been properly loaded within a rack tray. Users can be alerted when an error is found.

In another example, the system can perform a unload check to determine whether used consumables have been removed prior to system cleanup. For example, the system can utilize the camera 5208 to take images of racks or devices to detect whether consumables are present that should have been removed. In a particular example, the system can prevent an automated system cleaning from occurring when used consumables have not been removed from the system deck.

In another example illustrated in FIG. 53, the system can perform a tip check to determine proper attachment of the pipette tip to the pipette system. For example, a camera 5304 can take an image of a tip 5302. In a particular example, the camera 5304 can be angled to obtain a perspective view of the tip 5302. The angle can be between 1° and 20° relative to vertical, such as between 1° and 10° or even between 2° and 7°. Using the perspective view of the tip 5302, the camera and system can determine a width of the end of the tip and a length of the tip to determine whether the tip is disposed at an angle relative to the axis passing through the pipette system or to determine which tip size has been attached.

In addition, the vision system can be calibrated to determine a position of the track system in three directions. For example, as illustrated in FIG. 54, the system can include a calibration well 5402. An end of the pipette system can be positioned within the calibration well and images can be taken of the system when the pipette end is within the calibration well 5402. Additional images can be taken as the pipette system is moved up in a z-direction (vertical) while keeping x- and y-directions constant (horizontal).

For example, as illustrated in FIG. 55, a method 5500 includes directing the pipette instrument to a calibration well, as illustrated 5502. The pipette instrument can be directed to the calibration well manually or electronically. The calibration well represents a zero height in the z-direction. As a pipette is moved in a z-direction, as illustrated 5504, images of the calibration well are taken, as illustrated at 5506. The corresponding images and z-positions are used to calibrate the vertical positioning of the system, as illustrated 5508, to control vertical movement of the track system using the vision system.

Returning to FIG. 54, a further calibration plate 5404 can include calibration markings 5406. As illustrated in FIG. 54, the calibration markings 5406 are dark spots. Other calibration markings, such as crosses, lines, barcodes, or grids, can be used.

Figure 56:
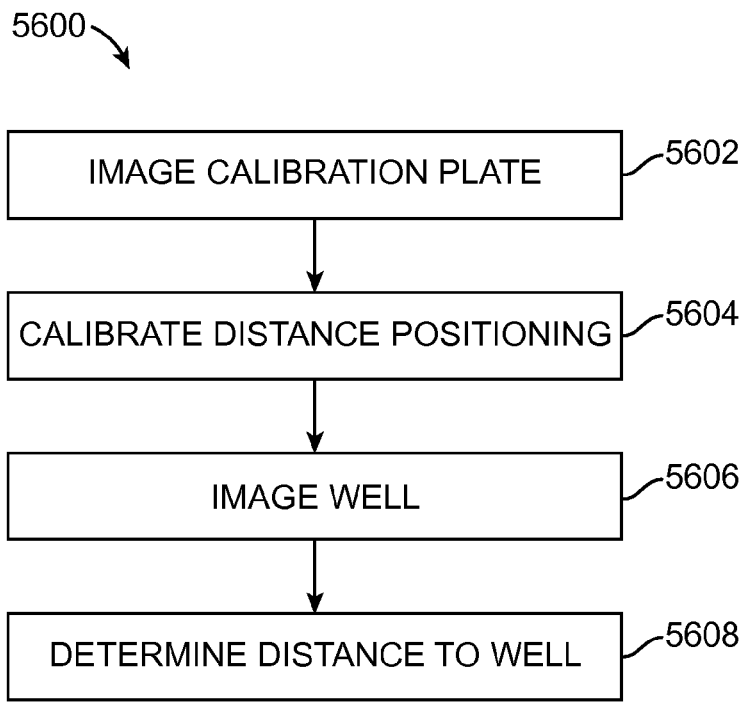

As illustrated in FIG. 56, a method for calibrating 5600 includes imaging a calibration plate, as illustrated 5602. Based on the angle of the camera, an image of the calibration plate may show distortions with on horizontal distance.

The image of the calibration plate can be used to calibrate distance positioning, as illustrated 5604. For example, the tubes or trays distant from the camera may appear distorted. Using the calibration, the camera can determine the distance to the tube or tray. For example, when moving to a well, the system the image the well, as illustrated 5606, and determine a distance to the well, as illustrated at 5608, using the calibrated distance positioning to assist in processing the image of the well. The system can then move to the well using the determined distance.

In a further example, the system can use images to calibrate positioning of the centrifuge rotor. For example, a centrifuge may be directed to a home index. The system can take an image of the rotor and determine an angular offset from a desired position. The angular offset can be used to determine rotational counts to move the system from the home index to a desired position. These counts can be stored within an encoder of the centrifuge. In such a manner, the centrifuge can be directed to a home index and then moved into a desired position.

In addition or alternatively, z-axis calibration can be conducted when a pipette tip is secured to the pipette system. For example, the end of the pipette tip can be determined by adjusting the height of the track system until the pipette tip touches a calibration surface. In particular example, the system can detect that a pipette tip touches the calibration surface by testing for a pressure change using the pipette system.

Figure 57:
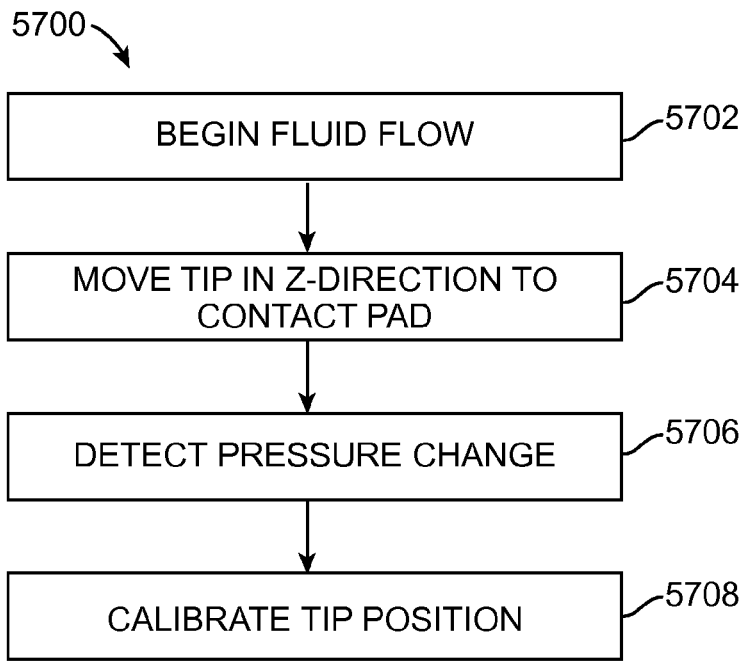

For example, the system may move to a pipette tip rack and the pipette system can be attached to a pipette tip. An image system can determine that the correct tip was attached and assess whether the tip is attached in a vertical position. The system can then move the pipette tip to a calibration point. As illustrated in FIG. 57, a method 5700 includes beginning a fluid flow through the pipette tip, as illustrated 5702. For example, the pipette system may draw or expel gas through the pipette tip. The system can then move the tip in the z-direction to a contact pad, as illustrated at 5704.

When a pressure change is detected by the pipette system, the system can stop moving in the z-direction, as illustrated at 5706. In particular, the fluid flow through the tip causes a pressure change when the tip approaches and contacts a calibration surface. For example, if the pipette system is expelling gas through the tip, the system experiences a pressure increase when the tip contacts the calibration surface. In another example, when the pipette system is drawing air through the pipette tip, the system may experience a decrease in pressure when the tip comes in contact with the calibration surface.

Using the position of the track system when the pressure change is detected, the system can calibrate the z-position of the end of the pipette tip, as illustrated 5708. In an example, the calibration surface can be a flat surface. The surface can be a hard surface or can be an elastomeric surface. In another example, the surface can be the bottom of a tube or well.

In a further embodiment, a method for preparing a sequencing device includes transferring an aqueous dispersion including amplified particles to an enrichment tube using a translation device coupled to a syringe pump, enriching the amplified particles, transferring the enriched amplified particles to a sequencing device disposed on a tray of a centrifuge device, and centrifuging the sequencing device.

The disclose system and method provide technical advantages including reduced variability within the amplification, enrichment, and loading procedures. Such a reduction in variation has a significant effect on the parameters associated with sequencing performance. In particular, such a device and associated methods provide improved numbers of AQ17 reads from a given sensor array.

In a first aspect, a method of calibrating a system includes attaching a pipette tip to a syringe pump coupled to a translation device, initiating fluid flow through the pipette tip, moving the pipette tip toward a contact surface with the translation device, and calibrating the system based on a position of the translation device when the syringe pump detects a pressure change.

In an example of the first aspect, the translation device can move the syringe pump in three orthogonal directions.

In another example of the first aspect and the above examples, initiating fluid flow includes drawing air through the pipette tip with the syringe pump. For example, the pressure change includes a decrease in pressure, the method further including stopping moving the pipette tip toward the contact surface when the decrease in pressure is detected.

In a further example of the first aspect and the above examples, initiating fluid flow includes expelling fluid through the pipette tip using the syringe pump. For example, the pressure change includes an increase in pressure, the method further including stopping moving the pipette tip toward the contact surface when the increase in pressure is detected.

In an additional example of the first aspect and the above examples, attaching the pipette tip to the syringe pump includes lowering a distal end of the syringe pump into the pipette tip using the translation device.

In another example of the first aspect and the above examples, the contact surface is an elastomeric surface.

In a further example of the first aspect and the above examples, the contact surface is in a tube or well.

In a second aspect, a centrifuge device includes a motor operable to spin in a first direction and in a second direction opposite the first direction and a rotor coupled to a motor. The rotor is to spin within a plane in the first direction or the second direction responsive to the motor. The rotor has a recess and an axle projecting from a side of the recess. The centrifuge device further includes a carrier slidably and pivotally coupled to the axle. The carrier includes a first tab on a first side and a second tab on a second side. The carrier is to slide along the axle and to rotate about the axle out of the plane and engage the rotor with the first tab at a first angle in response to the rotor spinning in the first direction. The carrier is to slide along the axle and to rotate about the axle out of the plane and engage the rotor with the second tab at a second angle in response to the rotor spinning in the second direction.

In an example of the second aspect, the carrier is configured to receive a sequencing component including two fluid ports. For example, the two fluid ports are to face inward toward an axis of spinning of the rotor. In another example, the centrifuge device further includes a fastener to secure the sequencing component to the carrier. In an example, the fastener includes elements to engage the two fluid ports of the sequencing component.

In another example of the second aspect and the above examples, the first angle is in a range of 70° to 110° relative to the plane. For example, the first angle is in a range of 80° to 95° relative to the plane.

In a further example of the second aspect and the above examples, the second angle is in a range of 20° to 65° relative to the plane. For example, the second angle is in a range of 35° to 50° relative to the plane.

In an additional example of the second aspect and the above examples, the axle extends at least partially across the recess, the carrier at least partially in the recess when the rotor is stationary.

In a third aspect, a method includes spinning a rotor within a plane in a first direction. A carrier is coupled to the rotor by an axle. The carrier slides along the axle and rotates about the axle to engage the rotor with a first tab at a first angle in response to the rotor spinning in the first direction. The method further includes spinning the rotor within the plane in a second direction. The carrier slides along the axle and rotates about the axle to engage the rotor with a second tab at a second angle in response to the rotor spinning in the second direction. The first angle is greater than the second angle.

In an example of the third aspect, the carrier is configured to receive a sequencing component including two fluid ports. For example, the two fluid ports are to face inward toward an axis of spinning of the rotor. In another example, the method further includes engaging a fastener to secure the sequencing component to the carrier. For example, the fastener includes elements to engage the two fluid ports of the sequencing component. In an additional example, the method further includes inserting a solution including polynucleotide beads in the sequencing component prior to spinning. In a particular example, a portion of the solution exits at least one of the two fluid ports when spinning at the second angle.

In another example of the third aspect and the above examples, the first angle is in a range of 70° to 110° relative to the plane. For example, the first angle is in a range of 80° to 95° relative to the plane.

In a further example of the third aspect and the above examples, the second angle is in a range of 20° to 65° relative to the plane. For example, the second angle is in a range of 35° to 50° relative to the plane.

In an additional example of the third aspect and the above examples, the axle extends at least partially across the recess, the carrier at least partially in the recess when the rotor is stationary.

In a fourth aspect, a centrifuge includes a rotor to spin within a plane, a carrier, an upper plate, and a first arm pivotally coupled at a first end to the upper plate. A second end of the first arm is pivotally coupled to the carrier. The centrifuge further includes a second arm pivotally coupled to the rotor at a first end. A second end of the second arm is pivotally coupled to the first arm at a position on the first arm between the first end and the second end of the first arm. An angle of the carrier relative to the plane changes responsive to position of the upper plate.

In an example of the fourth aspect, the method further includes an actuator coupled to the upper plate to move the upper plate in a direction normal to the plane.

In another example of the fourth aspect and the above examples, the carrier is configured to receive a sequencing component including two fluid ports. For example, the two fluid ports are to face inward toward an axis of spinning of the rotor. In another example, the centrifuge further includes a fastener to secure the sequencing component to the carrier. For example, the fastener includes elements to engage the two fluid ports of the sequencing component.

In a further example of the fourth aspect and the above examples, the centrifuge further includes a third arm and a fourth arm. The third arm is pivotally coupled to the upper plate at a first end of the third arm. A second end of the third arm is pivotally coupled to a first end of the fourth arm. A second end of the fourth arm is pivotally coupled to the rotor.

In a fifth aspect, a centrifuge includes a rotor to spin in a plane, a slinger positioned over a central axis of the rotor and including a receiving port and an arm including a distal opening in fluid communication with the receiving port, and a carrier block pivotally coupled to the rotor and including a receptacle for a tube. The carrier block weighted to position the tube in an approximate vertical position when the rotor is stationary and to position the tube at an angle with an opening of the tube directed to the distal opening of the slinger responsive to the rotor spinning.

In an example, the centrifuge further includes a lid. For example, the lid includes an opening, one edge of the opening sized to receive the tube and a second edge of the opening sized smaller than a lip of the tube.

In a sixth aspect, a method includes lowering a distal end of a pipette system to engage a pipette tip in a tray, raising the distal end, imaging the distal end with a camera, and comparing a characteristic derived from the image with an expected tip characteristic.

In an example, the characteristic is a width at the end of the pipette tip. In another example, the characteristic is indicative of a length of the pipette tip. In an additional example, the characteristic is indicative of an angle of the pipette tip relative to the syringe pump.

In another example, the camera is positioned to image at an angle relative to the vertical in a range of 1° to 10°.

In a seventh aspect, a system includes a syringe pump to couple to a pipette tip, a translation device to move the pipette tip, an enrichment system, and a centrifuge device. The enrichment system includes a mixing tube and a magnetic device movable relative to the mixing tube. The centrifuge device includes a rotor and a bucket to secure a sequencing device. The translation device is to position the pipette tip proximal to the mixing tube and proximal to the sequencing device.

In an eighth aspect, a method for preparing a sequencing device includes transferring an aqueous dispersion including amplified particles to an enrichment tube using a translation device coupled to a syringe pump, enriching the amplified particles, transferring the enriched amplified particles to a sequencing device disposed on a tray of a centrifuge device, and centrifuging the sequencing device.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive- or and not to an exclusive- or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A centrifuge device comprising:
 a motor operable to spin in a first direction and in a second direction opposite the first direction;
 a rotor coupled to a motor, the rotor to spin within a plane in the first direction or the second direction responsive to the motor, the rotor having a recess and an axle projecting from a side of the recess; and
 a carrier slidably and pivotally coupled to the axle, the carrier including a first tab on a first side and a second tab on a second side, the carrier to slide along the axle and to rotate about the axle out of the plane and engage the rotor with the first tab at a first angle in response to the rotor spinning in the first direction, the carrier to slide along the axle and to rotate about the axle out of the plane and engage the rotor with the second tab at a second angle in response to the rotor spinning in the second direction.

2. The centrifuge device of claim 1, wherein the carrier is configured to receive a sequencing component including two fluid ports.

3. The centrifuge device of claim 2, wherein the two fluid ports are to face inward toward an axis of spinning of the rotor.

4. The centrifuge device of claim 2, further comprising a fastener to secure the sequencing component to the carrier.

5. The centrifuge device of claim 4, wherein the fastener includes elements to engage the two fluid ports of the sequencing component.

6. The centrifuge device of claim 1, wherein the first angle is in a range of 70° to 110° relative to the plane.

7. The centrifuge device of claim 6, wherein the first angle is in a range of 80° to 95° relative to the plane.

8. The centrifuge device of claim 1, wherein the second angle is in a range of 20° to 65° relative to the plane.

9. The centrifuge device of claim 8, wherein the second angle is in a range of 35° to 50° relative to the plane.

10. The centrifuge device of claim 1, wherein the axle extends at least partially across the recess, the carrier at least partially in the recess when the rotor is stationary.

11. A method comprising:
 spinning a rotor within a plane in a first direction, a carrier coupled to the rotor by an axle, the carrier sliding along the axle in a second direction within the plane and rotating about the axle to engage the rotor with a first tab of the carrier at a first angle in response to the rotor spinning in the first direction; and
 spinning the rotor within the plane in the second direction, the carrier sliding along the axle in the first direction and rotating about the axle to engage the rotor with a second tab of the carrier at a second angle in response to the rotor spinning in the second direction, the first angle being greater than the second angle.

12. The method of claim 11, wherein the carrier is configured to receive a sequencing component including two fluid ports.

13. The method of claim 12, wherein the two fluid ports are to face inward toward an axis of spinning of the rotor.

14. The method of claim 13, further comprising engaging a fastener to secure the sequencing component to the carrier.

15. The method of claim 14, wherein the fastener includes elements to engage the two fluid ports of the sequencing component.

16. The method of claim 12, further comprising inserting a solution including polynucleotide beads in the sequencing component prior to spinning.

17. The method of claim 16, wherein a portion of the solution exits at least one of the two fluid ports when spinning at the second angle.

18. The method of claim 11, wherein the first angle is in a range of 70° to 110° relative to the plane.

19. The method of claim 11, wherein the second angle is in a range of 20° to 65° relative to the plane.

20. The method of claim 11, wherein the axle extends at least partially across a recess in the rotor, the carrier at least partially in the recess when the rotor is stationary.

* * * * *